US009479753B2

(12) United States Patent
Tsukagoshi et al.

(10) Patent No.: US 9,479,753 B2
(45) Date of Patent: Oct. 25, 2016

(54) IMAGE PROCESSING SYSTEM FOR MULTIPLE VIEWPOINT PARALLAX IMAGE GROUP

(75) Inventors: Shinsuke Tsukagoshi, Nasushiobara (JP); Takashi Tsutsumi, Sumida-ku (JP); Akira Taniguchi, Nerima-ku (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 25 days.

(21) Appl. No.: 13/552,056

(22) Filed: Jul. 18, 2012

(65) Prior Publication Data

US 2013/0021336 A1 Jan. 24, 2013

(30) Foreign Application Priority Data

Jul. 19, 2011 (JP) ................................. 2011-158140

(51) Int. Cl.
| | |
|---|---|
| *G06T 15/00* | (2011.01) |
| *H04N 13/00* | (2006.01) |
| *G02B 27/22* | (2006.01) |
| *H04N 13/04* | (2006.01) |
| *G02B 27/00* | (2006.01) |
| *A61B 6/00* | (2006.01) |

(52) U.S. Cl.
CPC ........... *H04N 13/0014* (2013.01); *A61B 6/462* (2013.01); *A61B 6/466* (2013.01); *A61B 6/469* (2013.01); *A61B 6/5223* (2013.01); *G02B 27/0093* (2013.01); *G02B 27/2214* (2013.01); *H04N 13/0404* (2013.01); *H04N 13/0445* (2013.01); *H04N 13/0484* (2013.01); *A61B 6/501* (2013.01)

(58) Field of Classification Search
CPC ..................................................... G06T 19/08
USPC ....................................................... 345/419
See application file for complete search history.

(56) References Cited

U.S. PATENT DOCUMENTS 6,771,262 B2 *  8/2004 Krishnan ....................... 345/424
7,567,648 B2 *  7/2009 Tsubaki et al. ................. 378/41
(Continued)

FOREIGN PATENT DOCUMENTS

| JP | 2001-42259 A | 2/2001 |
| JP | 2006-101329 A | 4/2006 |

(Continued)

OTHER PUBLICATIONS

Office Action issued on Apr. 5, 2016 in Japanese Patent Application No. 2012-131979.

*Primary Examiner* — Jacinta M Crawford
*Assistant Examiner* — Shivang Patel
(74) *Attorney, Agent, or Firm* — Oblon, McClelland, Maier & Neustadt, L.L.P.

(57) ABSTRACT

An image processing system according to an embodiment includes a stereoscopic display device, a receiving unit, and a display controller. The stereoscopic display device displays a stereoscopic image that is capable of being viewed stereoscopically using a parallax image group as a plurality of parallax images generated by performing rendering processing on volume data as three-dimensional medical image data. The receiving unit receives a region of interest in the stereoscopic image. The display controller causes the stereoscopic display device to display the parallax image group that has been generated by performing the rendering processing on the volume data based on a plurality of viewpoint positions of which sight line directions intersect with one another at a position of the volume data that corresponds to the region of interest received by the receiving unit.

14 Claims, 18 Drawing Sheets

(56) References Cited

U.S. PATENT DOCUMENTS

2011/0235066 A1* 9/2011 Sakuragi ............... G06T 7/0022
                                                        358/1.6
2012/0245465 A1* 9/2012 Hansegard et al. .......... 600/443

FOREIGN PATENT DOCUMENTS

JP          4015090        9/2007
JP       2008-532062 A     8/2008

* cited by examiner

INFRARED-RAY RECEIVING UNIT
INFRARED-RAY EMITTING UNIT
SHUTTER GLASSES

POLARIZATION PLATE
LIQUID CRYSTAL LAYER
VOLTAGE: OFF
VOLTAGE: ON
TRANSMITTING STATE
LIGHT SHIELDING STATE
POLARIZATION PLATE

IMAGE PROCESSING SYSTEM FOR MULTIPLE VIEWPOINT PARALLAX IMAGE GROUP

CROSS-REFERENCE TO RELATED APPLICATIONS

This application is based upon and claims the benefit of priority from Japanese Patent Application No. 2011-158140, filed on Jul. 19, 2011; the entire contents of which are incorporated herein by reference.

FIELD

Embodiments described herein relate generally to an image processing system, an image processing device, an image processing method, and a medical image diagnostic device.

BACKGROUND

Conventionally known is a technique of displaying two images shot from two viewpoints on a monitor so as to display an image that can be viewed stereoscopically by a user using a dedicated device such as stereoscopic glasses. Furthermore, in recent years, also known is a technique of displaying images (for example, nine images) shot from a plurality of viewpoints on a monitor using a light beam controller such as a lenticular lens so as to display an image that can be also viewed stereoscopically by a user with naked eyes. A plurality of images to be displayed on a monitor that can be viewed stereoscopically are generated by estimating depth information of an image shot from one viewpoint and performing image processing using the estimated information in some cases.

As medical image diagnostic devices such as X-ray computed tomography (CT) devices, magnetic resonance imaging (MRI) devices, and ultrasonography devices, devices that can generate three-dimensional medical image data (hereinafter, volume data) have been put into practice. Such a medical image diagnostic device generates a flat image for display by executing various pieces of image processing on volume data and displays the generated flat image on a general-purpose monitor. For example, the medical image diagnostic device executes volume rendering processing on volume data so as to generate a two-dimensional rendering image on which three-dimensional information for a subject has been reflected, and displays the generated rendering image on the general-purpose monitor.

DETAILED DESCRIPTION

An image processing system according to an embodiment includes a stereoscopic display device, a receiving unit, and a display controller. The stereoscopic display device displays a stereoscopic image that can be viewed stereoscopically using a parallax image group that is a plurality of parallax images generated by performing rendering processing on volume data as three-dimensional medical image data. The receiving unit receives a region of interest in the stereoscopic image. The display controller causes the stereoscopic display device to display the parallax image group generated by performing the rendering processing on the volume data based on a plurality of viewpoint positions of which sight line directions intersect with one another at a position of the volume data that corresponds to the region of interest received by the receiving unit.

Hereinafter, embodiments of the image processing system, an image processing device, an image processing method, and a medical image diagnostic device are described in detail with reference to accompanying drawings. In the following, an image processing system including a workstation with a function as an image processing apparatus is described as an embodiment. Here, the terminology used in the following embodiments is described. A "parallax image group" refers to an image group which is generated by performing a volume rendering process on volume data while moving a point-of-view position by a predetermined parallactic angle at a time. In other words, the "parallax image group" is configured with a plurality of "parallax images" having different "point-of-view positions." Further, a "parallactic angle" refers to an angle determined by an adjacent point-of-view position among point-of-view positions set to generate the "parallax image group" and a predetermined position in a space (the center of a space) represented by volume data. Further, a "parallax number" refers to the number of "parallax images" necessary to implement a stereoscopic view by a stereoscopic display monitor. Further, a "nine-parallax image" described in the following refers to a "parallax image group" consisting of nine "parallax images." Furthermore, a "two-parallax image" described in the following refers to a "parallax image group" consisting of two "parallax images."

First Embodiment

First, a configuration example of an image processing system according to a first embodiment will be described.

Figure 1:
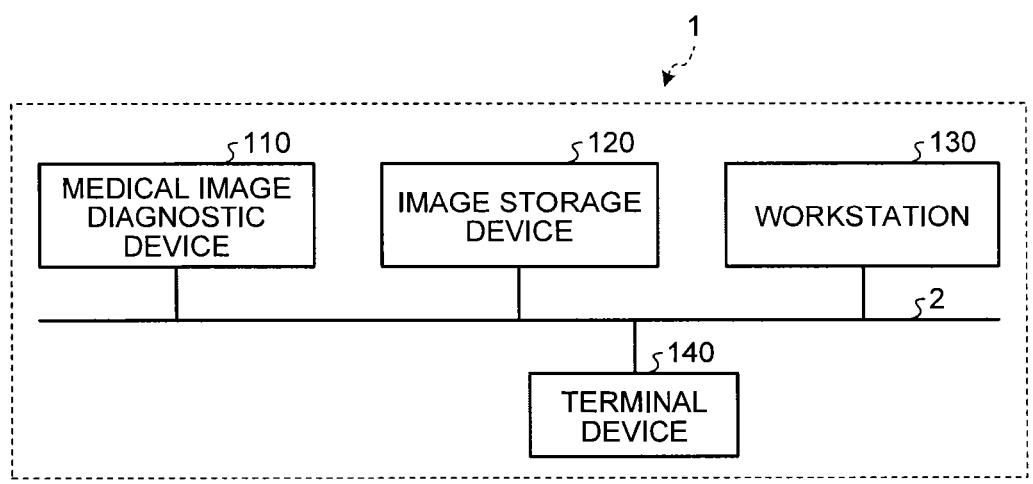
FIG. 1 is a diagram for explaining a configuration example of an image processing system according to a first embodiment.

FIG. 1 is a diagram for describing a configuration example of an image processing system according to the first embodiment.

As illustrated in FIG. 1, an image processing system 1 according to the first embodiment includes a medical image diagnostic device 110, an image storage device 120, a workstation 130, and a terminal device 140. The respective devices illustrated in FIG. 1 are connected to directly or indirectly communicate one another, for example, via a hospital Local Area Network (LAN) 2 installed in a hospital. For example, when a Picture Archiving and Communication System (PACS) is introduced into the image processing system 1, the respective devices exchange a medical image or the like with one another according to a Digital Imaging and Communications in Medicine (DICOM) standard.

The image processing system 1 provides an observer, who works in the hospital such as a doctor or a laboratory technician, with a stereoscopic image which is an image stereoscopically viewable to the observer by generating a parallax image group based on volume data which is 3D medical image data generated by the medical image diagnostic device 110 and then causing the parallax image group to be displayed on a monitor with a stereoscopic view function. Specifically, in the first embodiment, the workstation 130 performs a variety of image processing on volume data and generates a parallax image group. Each of the workstation 130 and the terminal device 140 includes a monitor with a stereoscopic view function, and displays a stereoscopic image to a user by displaying the parallax image group generated by the workstation 130 through the monitor. The image storage device 120 stores volume data generated by the medical image diagnostic device 110 and the parallax image group generated by the workstation 130. For example, the workstation 130 or the terminal device 140 acquires the volume data or the parallax image group from the image storage device 120, executes arbitrary image processing on the acquired volume data or the acquired parallax image group, and causes the parallax image group to be displayed on the monitor. The respective devices will be described below in order.

The medical image diagnostic device 110 is an X-ray diagnostic device, an X-ray Computed Tomography (CT) device, a Magnetic Resonance Imaging (MRI) device, an ultrasonic diagnostic device, a Single Photon Emission Computed Tomography (SPECT) device, a Positron Emission computed Tomography (PET) device, a SPECT-CT device in which a SPECT device is integrated with an X-ray CT device, a PET-CT device in which a PET device is integrated with an X-ray CT device, a device group thereof, or the like. The medical image diagnostic device 110 according to the first embodiment can generate 3D medical image data (volume data).

Specifically, the medical image diagnostic device 110 according to the first embodiment captures a subject, and generates volume data. For example, the medical image diagnostic device 110 generates volume data such that it collects data such as projection data or an MR signal by capturing a subject, and then reconstructs medical image data including a plurality of axial planes along a body axis direction of a subject based on the collected data. For example, when the medical image diagnostic device 110 reconstructs medical image data of 500 axial planes, a medical image data group of 500 axial planes is used as volume data. Alternatively, projection data or an MR signal of a subject captured by the medical image diagnostic device 110 may be used as volume data.

The medical image diagnostic device 110 according to the first embodiment transmits the generated volume data to the image storage device 120. When the medical image diagnostic device 110 transmits the volume data to the image storage device 120, the medical image diagnostic device 110 transmits supplementary information such as a patient ID identifying a patient, an inspection ID identifying an inspection, a device ID identifying the medical image diagnostic device 110, and a series ID identifying single shooting by the medical image diagnostic device 110, for example.

The image storage device 120 is a database that stores a medical image. Specifically, the image storage device 120 according to the first embodiment receives the volume data from the medical image diagnostic device 110, and stores the received volume data in a predetermined storage unit. Further, in the first embodiment, the workstation 130 generates a parallax image group based on the volume data, and transmits the generated parallax image group to the image storage device 120. Thus, the image storage device 120 stores the parallax image group transmitted from the workstation 130 in a predetermined storage unit. Further, in the present embodiment, the workstation 130 capable of storing a large amount of images may be used, and in this case, the image storage device 120 illustrated in FIG. 1 may be incorporated with the workstation 130 illustrated in FIG. 1. In other words, in the present embodiment, the volume data or the parallax image group may be stored in the workstation 130.

Further, in the first embodiment, the volume data or the parallax image group stored in the image storage device 120 is stored in association with the patient ID, the inspection ID, the device ID, the series ID, and the like. Thus, the workstation 130 or the terminal device 140 performs a search using the patient ID, the inspection ID, the device ID, the series ID, or the like, and acquires necessary volume data or a necessary parallax image group from the image storage device 120.

The workstation 130 is an image processing apparatus that performs image processing on a medical image. Specifically, the workstation 130 according to the first embodiment performs various rendering processes on the volume data acquired from the image storage device 120, and generates a parallax image group.

Further, the workstation 130 according to the first embodiment includes a monitor (which is referred to as a "stereoscopic display monitor" or "stereoscopic image display device") capable of displaying a stereoscopic image as a display unit. The workstation 130 generates a parallax image group and causes the generated parallax image group to be displayed on the stereoscopic display monitor. Thus, an operator of the workstation 130 can perform an operation of generating a parallax image group while checking a stereoscopically viewable stereoscopic image displayed on the stereoscopic display monitor.

Further, the workstation 130 transmits the generated parallax image group to the image storage device 120 or the terminal device 140. The workstation 130 transmits the supplementary information such as the patient ID, the inspection ID, the device ID, and the series ID, for example, when transmitting the parallax image group to the image storage device 120 or the terminal device 140. As supplementary information transmitted when the parallax image group is transmitted to the image storage device 120, supplementary information related to the parallax image group is further included. Examples of the supplementary information related to the parallax image group include the number of parallax images (for example, "9") and the resolution of a parallax image (for example, "466×350 pixels."

The terminal device 140 is a device that allows a doctor or a laboratory technician who works in the hospital to view a medical image. Examples of the terminal device 140 include a Personal Computer (PC), a tablet-type PC, a Personal Digital Assistant (PDA), and a portable telephone, which are operated by a doctor or a laboratory technician who works in the hospital. Specifically, the terminal device 140 according to the first embodiment includes a stereoscopic display monitor as a display unit. Further, the terminal device 140 acquires a parallax image group from the image storage device 120, and causes the acquired parallax image group to be displayed on the stereoscopic display monitor. As a result, a doctor or a laboratory technician who is an observer can view a stereoscopically viewable medical image. Alternatively, the terminal device 140 may be an arbitrary information processing terminal connected with a stereoscopic display monitor as an external device.

Here, the stereoscopic display monitor included in the workstation 130 or the terminal device 140 will be described. A general-purpose monitor which is currently most widely used two dimensionally displays a two-dimensional (2D) image and hardly performs a 3D display on a 2D image. If an observer desires a stereoscopic view to be displayed on the general-purpose monitor, a device that outputs an image to the general-purpose monitor needs to parallel-display a two-parallax image stereoscopically viewable to an observer through a parallel method or an intersection method. Alternatively, a device that outputs an image to the general-purpose monitor needs to display an image stereoscopically viewable to an observer through a color-complementation method using glasses in which a red cellophane is attached to a left-eye portion and a blue cellophane is attached to a right-eye portion.

Meanwhile, there are stereoscopic display monitors that allow a two-parallax image (which is also referred to as a "binocular parallax image") to be stereoscopically viewed using a dedicated device such as stereoscopic glasses.

Figure 2A:
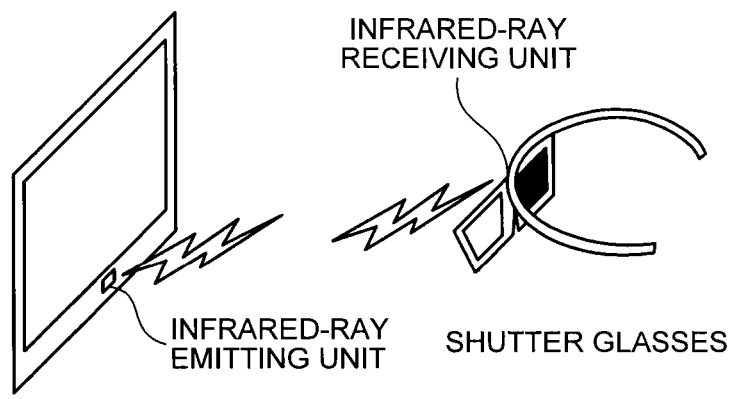
FIG. 2A and FIG. 2B are views for explaining an example of a stereoscopic display monitor on which stereoscopic display is performed using two-parallax images.
Figure 2B:
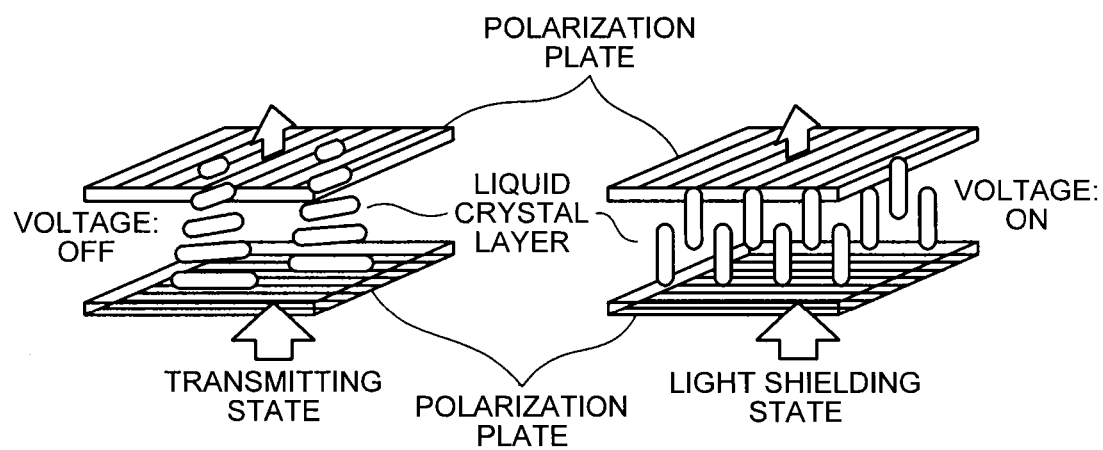

FIGS. 2A and 2B are diagrams for describing an example of a stereoscopic display monitor that performs a stereoscopic display based on a two-parallax image. In the example illustrated in FIGS. 2A and 2B, the stereoscopic display monitor performs a stereoscopic display by a shutter method, and shutter glasses are used as stereoscopic glasses worn by an observer who observes the monitor. The stereoscopic display monitor alternately outputs a two-parallax image in the monitor. For example, the monitor illustrated in FIG. 2A alternately outputs a left-eye image and a right-eye image with 120 Hz. As illustrated in FIG. 2A, the monitor includes an infrared-ray output unit, and controls an output of an infrared ray according to a timing at which images are switched.

The infrared ray output from the infrared-ray output unit is received by an infrared-ray receiving unit of the shutter glasses illustrated in FIG. 2A. A shutter is mounted to each of right and left frames of the shutter glasses, and the shutter glasses alternately switch a transmission state and a light shielding state of the right and left shutters according to a timing at which the infrared-ray receiving unit receives the infrared ray. A switching process of a transmission state and a light shielding state of the shutter will be described below.

As illustrated in FIG. 2B, each shutter includes an incident side polarizing plate and an output side polarizing plate, and further includes a liquid crystal layer disposed between the incident side polarizing plate and the output side polarizing plate. The incident side polarizing plate and the output side polarizing plate are orthogonal to each other as illustrated in FIG. 2B. Here, as illustrated in FIG. 2B, in an OFF state in which a voltage is not applied, light has passed through the incident side polarizing plate rotates at 90° due to an operation of the liquid crystal layer, and passes through the output side polarizing plate. In other words, the shutter to which a voltage is not applied becomes a transmission state.

Meanwhile, as illustrated in FIG. 2B, in an ON state in which a voltage is applied, a polarization rotation operation caused by liquid crystal molecules of the liquid crystal layer does not work, and thus light having passed through the incident side polarizing plate is shielded by the output side polarizing plate. In other words, the shutter to which a voltage is applied becomes a light shielding state.

In this regard, for example, the infrared-ray output unit outputs the infrared ray during a time period in which the left-eye image is being displayed on the monitor. Then, during a time period in which the infrared ray is being received, the infrared-ray receiving unit applies a voltage to the right-eye shutter without applying a voltage to the left-eye shutter. Through this operation, as illustrated in FIG. 2A, the right-eye shutter becomes the light shielding state, and the left-eye shutter becomes the transmission state, so that the left-eye image is incident to the left eye of the observer. Meanwhile, during a time period in which the right-eye image is being displayed on the monitor, the infrared-ray output unit stops an output of the infrared ray. Then, during a time period in which the infrared ray is not being received, the infrared-ray receiving unit applies a voltage to the left-eye shutter without applying a voltage to the right-eye shutter. Through this operation, the left-eye shutter becomes the light shielding state, and the right-eye shutter becomes the transmission state, so that the right-eye image is incident to the right eye of the observer. As described above, the stereoscopic display monitor illustrated in FIGS. 2A and 2B causes an image stereoscopically viewable to the observer to be displayed by switching an image to be displayed on the monitor in conjunction with the state of the shutter. A monitor employing a polarizing glasses method other than the shutter method is also known as the stereoscopic display monitor that allows a two-parallax image to be stereoscopically viewed.

Further, a stereoscopic display monitor that allows an observer to stereoscopically view a multi-parallax image with the naked eyes such as a nine-parallax image using a light beam controller such as a lenticular lens has been recently put to practical. This kind of stereoscopic display monitor makes a stereoscopic view possible by binocular parallax, and further makes a stereoscopic view possible by kinematic parallax in which an observed video changes with the movement of a point of view of an observer.

Figure 3:
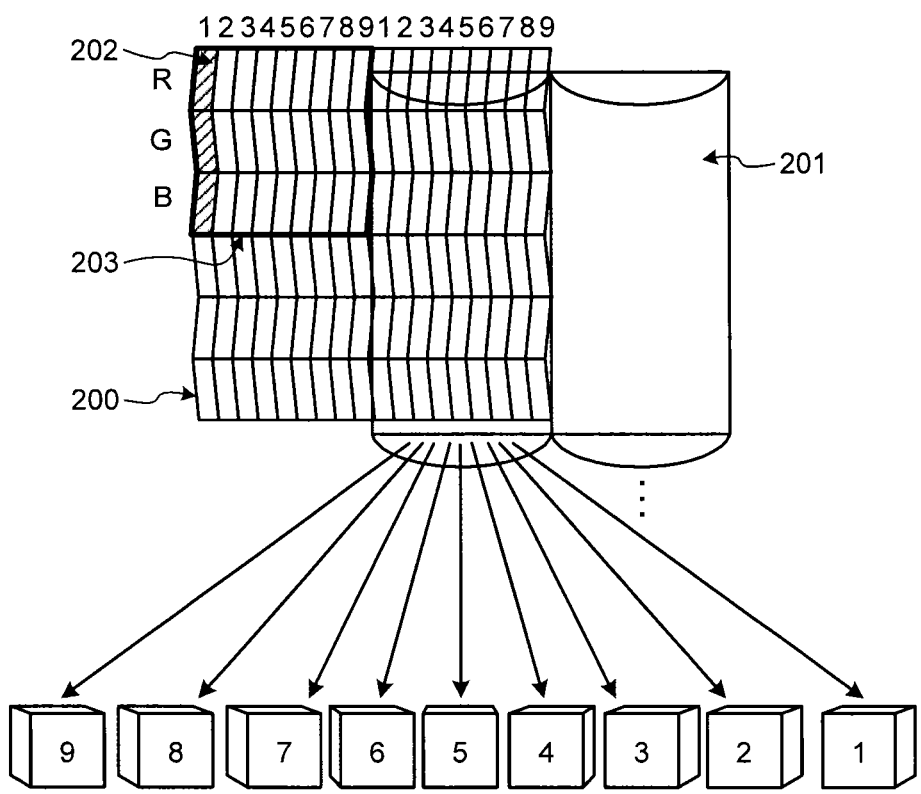
FIG. 3 is a view for explaining an example of a stereoscopic display monitor on which stereoscopic display is performed using nine-parallax images.

FIG. 3 is a diagram for describing an example of a stereoscopic display monitor that performs a stereoscopic display based on a nine-parallax image. In the stereoscopic display monitor illustrated in FIG. 3, a light beam controller is arranged in front of a planar display surface 200 such as a liquid crystal panel. For example, in the stereoscopic display monitor illustrated in FIG. 3, a vertical lenticular sheet 201 including an optical opening that extends in a vertical direction is attached to the front surface of the display surface 200 as the light beam controller. In the example illustrated in FIG. 3, the vertical lenticular sheet 201 is attached such that a convex portion thereof serves as the front surface, but the vertical lenticular sheet 201 may be attached such that a convex portion thereof faces the display surface 200.

As illustrated in FIG. 3, in the display surface 200, an aspect ratio is 3:1, and pixels 202 each of which includes three sub-pixels of red (R), green (G), and blue (B) arranged in a longitudinal direction are arranged in the form of a matrix. The stereoscopic display monitor illustrated in FIG. 3 converts a nine-parallax image including nine images into an interim image arranged in a predetermined format (for example, in a lattice form), and outputs the interim image to the display surface 200. In other words, the stereoscopic display monitor illustrated in FIG. 3 allocates nine pixels at the same position in the nine-parallax image to the pixels 202 of nine columns, respectively, and then performs an output. The pixels 202 of nine columns become a unit pixel group 203 to simultaneously display nine images having different point-of-view positions.

The nine-parallax image simultaneously output as the unit pixel group 203 in the display surface 200 is radiated as parallel light through a Light Emitting Diode (LED) backlight, and further radiated in multiple directions through the vertical lenticular sheet 201. As light of each pixel of the nine-parallax image is radiated in multiple directions, lights incident to the left eye and the right eye of the observer change in conjunction with the position (the position of the point of view) of the observer. In other words, depending on an angle at which the observer views, a parallax image incident to the right eye differs in a parallactic angle from a parallax image incident to the left eye. Through this operation, the observer can stereoscopically view a shooting target, for example, at each of nine positions illustrated in FIG. 3. For example, the observer can stereoscopically view, in a state in which the observer directly faces a shooting target, at the position of "5" illustrated in FIG. 3, and can stereoscopically view, in a state in which a direction of a shooting target is changed, at the positions other than "5" illustrated in FIG. 3. The stereoscopic display monitor illustrated in FIG. 3 is merely an example. The stereoscopic display monitor that displays the nine-parallax image may include a horizontal stripe liquid crystal of "RRR - - - , GGG - - - , and BBB - - - " as illustrated in FIG. 3 or may include a vertical stripe liquid crystal of "RGBRGB - - - ." Further, the stereoscopic display monitor illustrated in FIG. 3 may be of a vertical lens type in which a lenticular sheet is vertical as illustrated in FIG. 3 or may be of an oblique lens type in which a lenticular sheet is oblique.

The configuration example of the image processing system 1 according to the first embodiment has been briefly described so far. An application of the image processing system 1 described above is not limited to a case in which the PACS is introduced. For example, the image processing system 1 is similarly applied even to a case in which an electronic chart system for managing an electronic chart with a medical image attached thereto is introduced. In this case, the image storage device 120 serves as a database for managing an electronic chart. Further, for example, the image processing system 1 is similarly applied even to a case in which a Hospital Information System (HIS) or Radiology Information System (RIS) is introduced. Further, the image processing system 1 is not limited to the above-described configuration example. A function or an assignment of each device may be appropriately changed according to an operation form.

Figure 4:
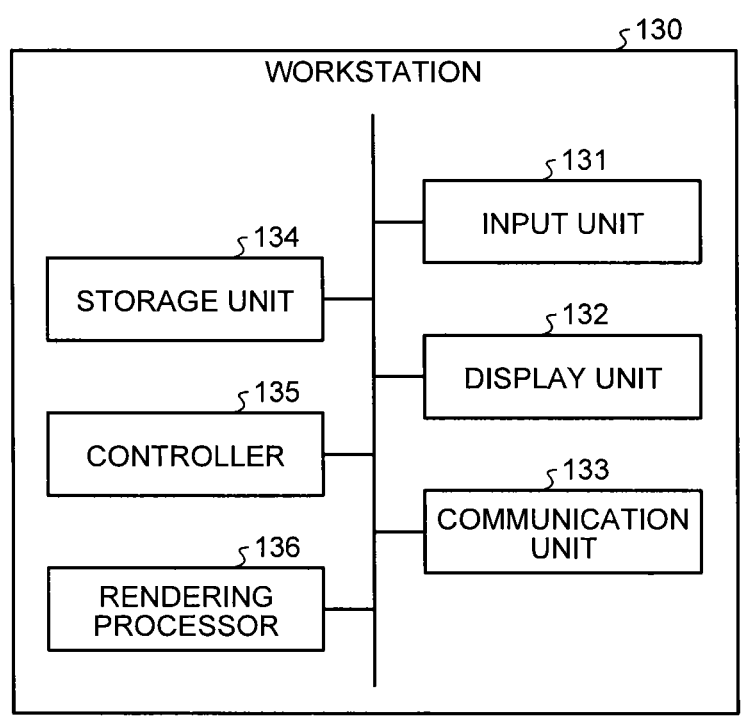
FIG. 4 is a diagram for explaining a configuration example of a workstation in the first embodiment.

Next, a configuration example of a workstation according to the first embodiment will be described with reference to FIG. 4. FIG. 4 is a diagram for describing a configuration example of a workstation according to the first embodiment. In the following, a "parallax image group" refers to an image group for a stereoscopic view generated by performing a volume rendering process on volume data. Further, a "parallax image" refers to each of images that configure the "parallax image group." In other words, the "parallax image group" is configured with a plurality of "parallax images" having different point-of-view positions.

The workstation 130 according to the first embodiment is a high-performance computer appropriate to image processing or the like, and includes an input unit 131, a display unit 132, a communication unit 133, a storage unit 134, a control unit 135, and a rendering processing unit 136 as illustrated in FIG. 4. In the following, a description will be made in connection with an example in which the workstation 130 is a high-performance computer appropriate to image processing or the like. However, the workstation 130 is not limited to this example, and may be an arbitrary information processing device. For example, the workstation 130 may be an arbitrary personal computer.

The input unit 131 includes a mouse, a keyboard, a trackball, or the like, and receives various operations which an operator has input on the workstation 130. Specifically, the input unit 131 according to the first embodiment receives an input of information used to acquire volume data which is a target of the rendering process from the image storage device 120. For example, the input unit 131 receives an input of the patient ID, the inspection ID, the device ID, the series ID, or the like. Further, the input unit 131 according to the first embodiment receives an input of a condition (hereinafter, referred to as a "rendering condition") related to the rendering process.

The display unit 132 includes a liquid crystal panel serving as a stereoscopic display monitor, and displays a variety of information. Specifically, the display unit 132 according to the first embodiment displays a Graphical User Interface (GUI), which is used to receive various operations from the operator, a parallax image group, or the like. The communication unit 133 includes a Network Interface Card (NIC) or the like and performs communication with other devices.

The storage unit 134 includes a hard disk, a semiconductor memory device, or the like, and stores a variety of information. Specifically, the storage unit 134 according to the first embodiment stores the volume data acquired from the image storage device 120 through the communication unit 133. Further, the storage unit 134 according to the first embodiment stores volume data which is under the rendering process, a parallax image group generated by the rendering process, or the like.

The control unit 135 includes an electronic circuit such as a Central Processing Unit (CPU), a Micro Processing Unit (MPU), or a Graphics Processing Unit (GPU) or an integrated circuit such as an Application Specific Integrated Circuit (ASIC) or a Field Programmable Gate Array (FPGA). The control unit 135 controls the workstation 130 in general.

For example, the control unit 135 according to the first embodiment controls a display of the GUI on the display unit 132 or a display of a parallax image group. Further, for example, the control unit 135 controls transmission/reception of the volume data or the parallax image group to/from the image storage device 120, which is performed through the communication unit 133. Further, for example, the control unit 135 controls the rendering process performed by the rendering processing unit 136. Further, for example, the control unit 135 controls an operation of reading volume data from the storage unit 134 or an operation of storing a parallax image group in the storage unit 134.

The rendering processing unit 136 performs various rendering processes on volume data acquired from the image storage device 120 under control of the control unit 135, and thus generates a parallax image group. Specifically, the rendering processing unit 136 according to the first embodiment reads volume data from the storage unit 134, and first performs pre-processing on the volume data. Next, the rendering processing unit 136 performs a volume rendering process on the pre-processed volume data, and generates a parallax image group. Subsequently, the rendering processing unit 136 generates a 2D image in which a variety of information (a scale, a patient name, an inspection item, and the like) is represented, and generates a 2D output image by superimposing the 2D image on each parallax image group. Then, the rendering processing unit 136 stores the generated parallax image group or the 2D output image in the storage unit 134. Further, in the first embodiment, the rendering process refers to the entire image processing performed on the volume data, and the volume rendering process a process of generating a 2D image in which 3D information is reflected during the rendering process. For example, the medical image generated by the rendering process corresponds to a parallax image.

Figure 5:
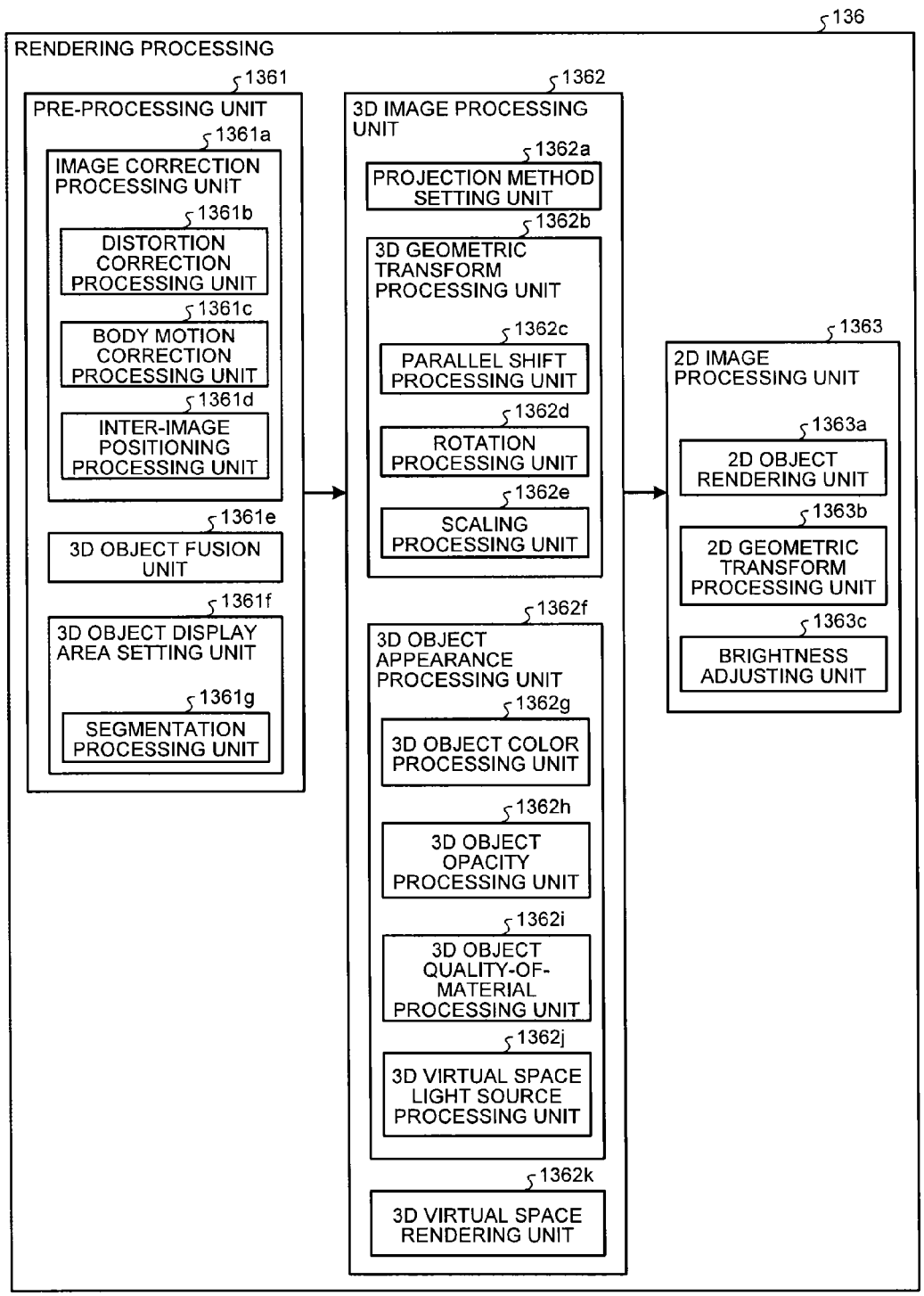
FIG. 5 is a diagram for explaining a configuration example of a rendering processor as illustrated in FIG. 4.

FIG. 5 is a diagram for describing a configuration example of the rendering processing unit illustrated in FIG. 4. As illustrated in FIG. 5, the rendering processing unit 136 includes a pre-processing unit 1361, a 3D image processing unit 1362, and a 2D image processing unit 1363. The pre-processing unit 1361 performs pre-processing on volume data. The 3D image processing unit 1362 generates a parallax image group from pre-processed volume data. The 2D image processing unit 1363 generates a 2D output image in which a variety of information is superimposed on a parallax image group. The respective units will be described below in order.

The pre-processing unit 1361 is a processing unit that performs a variety of pre-processing when performing the rendering process on volume data, and includes an image correction processing unit 1361a, a 3D object fusion unit 1361e, and a 3D object display area setting unit 1361f.

The image correction processing unit 1361a is a processing unit that performs an image correction process when processing two types of volume data as one volume data, and includes a distortion correction processing unit 1361b, a body motion correction processing unit 1361c, and an inter-image positioning processing unit 1361d as illustrated in FIG. 5. For example, the image correction processing unit 1361a performs an image correction process when processing volume data of a PET image generated by a PET-CT device and volume data of an X-ray CT image as one volume data. Alternatively, the image correction processing unit 1361a performs an image correction process when processing volume data of a T1-weighted image and volume data of a T2-weighted image which are generated by an MRI device as one volume data.

Further, the distortion correction processing unit 1361b corrects distortion of individual volume data caused by a collection condition at the time of data collection by the medical image diagnostic device 110. Further, the body motion correction processing unit 1361c corrects movement caused by body motion of a subject during a data collection time period used to generate individual volume data. Further, the inter-image positioning processing unit 1361d performs positioning (registration), for example, using a cross correlation method between two pieces of volume data which have been subjected to the correction processes by the distortion correction processing unit 1361b and the body motion correction processing unit 1361c.

The 3D object fusion unit 1361e performs the fusion of a plurality of volume data which have been subjected to the positioning by the inter-image positioning processing unit 1361d. Further, the processes performed by the image correction processing unit 1361a and the 3D object fusion unit 1361e may not be performed when the rendering process is performed on single volume data.

The 3D object display area setting unit 1361f is a processing unit that sets a display area corresponding to a display target organ designated by an operator, and includes a segmentation processing unit 1361g. The segmentation processing unit 1361g is a processing unit that extracts an organ, such as a heart, a lung, or a blood vessel, which is designated by the operator, for example, by an area extension technique based on a pixel value (voxel value) of volume data.

Further, the segmentation processing unit 1361g does not perform the segmentation process when a display target organ has not been designated by the operator. Further, the segmentation processing unit 1361g extracts a plurality of corresponding organs when a plurality of display target organs are designated by the operator. Further, the process performed by the segmentation processing unit 1361g may be re-executed at a fine adjustment request of the operator who has referred to a rendering image.

The 3D image processing unit 1362 performs the volume rendering process on the pre-processed volume data which has been subjected to the process performed by the pre-processing unit 1361. As processing units for performing the volume rendering process, the 3D image processing unit 1362 includes a projection method setting unit 1362a, a 3D geometric transform processing unit 1362b, a 3D object appearance processing unit 1362f, and a 3D virtual space rendering unit 1362k.

The projection method setting unit 1362a determines a projection method for generating a parallax image group. For example, the projection method setting unit 1362a determines whether the volume rendering process is to be executed using a parallel projection method or a perspective projection method.

The 3D geometric transform processing unit 1362b is a processing unit that determines information necessary to perform 3D geometric transform on volume data which is to be subjected to the volume rendering process, and includes a parallel shift processing unit 1362c, a rotation processing unit 1362d, and a scaling processing unit 1362e. The parallel shift processing unit 1362c is a processing unit that determines a shift amount to shift volume data in parallel when a point-of-view position is shifted in parallel at the time of the volume rendering process. The rotation processing unit

1362d is a processing unit that determines a movement amount for rotationally moving volume data when a point-of-view position is rotationally moved at the time of the volume rendering process. Further, the scaling processing unit 1362e is a processing unit that determines an enlargement ratio or a reduction ratio of volume data when it is requested to enlarge or reduce a parallax image group.

The 3D object appearance processing unit 1362f includes a 3D object color processing unit 1362g, a 3D object opacity processing unit 1362h, a 3D object quality-of-material processing unit 1362i, and a 3D virtual space light source processing unit 1362j. The 3D object appearance processing unit 1362f performs a process of determining a display form of a parallax image group to be displayed through the above processing units, for example, according to the operator's request.

The 3D object color processing unit 1362g is a processing unit that determines a color colored to each area segmented from volume data. The 3D object opacity processing unit 1362h is a processing unit that determines opacity of each voxel configuring each area segmented from volume data. In volume data, an area behind an area having opacity of "100%" is not represented in a parallax image group. Further, in volume data, an area having opacity of "0%" is not represented in a parallax image group.

The 3D object quality-of-material processing unit 1362i is a processing unit that determines the quality of a material of each area segmented from volume data and adjusts the texture when the area is represented. The 3D virtual space light source processing unit 1362j is a processing unit that determines the position or the type of a virtual light source installed in a 3D virtual space when the volume rendering process is performed on volume data. Examples of the type of a virtual light source include a light source that emits a parallel beam from infinity and a light source that emits a radial beam from a point of view.

The 3D virtual space rendering unit 1362k performs the volume rendering process on volume data, and generates a parallax image group. Further, the 3D virtual space rendering unit 1362k uses a variety of information, which is determined by the projection method setting unit 1362a, the 3D geometric transform processing unit 1362b, and the 3D object appearance processing unit 1362f, as necessary when the volume rendering process is performed.

Here, the volume rendering process performed by the 3D virtual space rendering unit 1362k is performed according to the rendering condition. For example, the parallel projection method or the perspective projection method may be used as the rendering condition. Further, for example, a reference point-of-view position, a parallactic angle, and a parallax number may be used as the rendering condition. Further, for example, a parallel shift of a point-of-view position, a rotational movement of a point-of-view position, an enlargement of a parallax image group, and a reduction of a parallax image group may be used as the rendering condition. Further, for example, a color colored, transparency, the texture, the position of a virtual light source, and the type of virtual light source may be used as the rendering condition. The rendering condition may be input by the operator through the input unit 131 or may be initially set. In either case, the 3D virtual space rendering unit 1362k receives the rendering condition from the control unit 135, and performs the volume rendering process on volume data according to the rendering condition. Further, at this time, the projection method setting unit 1362a, the 3D geometric transform processing unit 1362b, and the 3D object appearance processing unit 1362f determine a variety of necessary information according to the rendering condition, and thus the 3D virtual space rendering unit 1362k generates a parallax image group using a variety of information determined.

Figure 6:
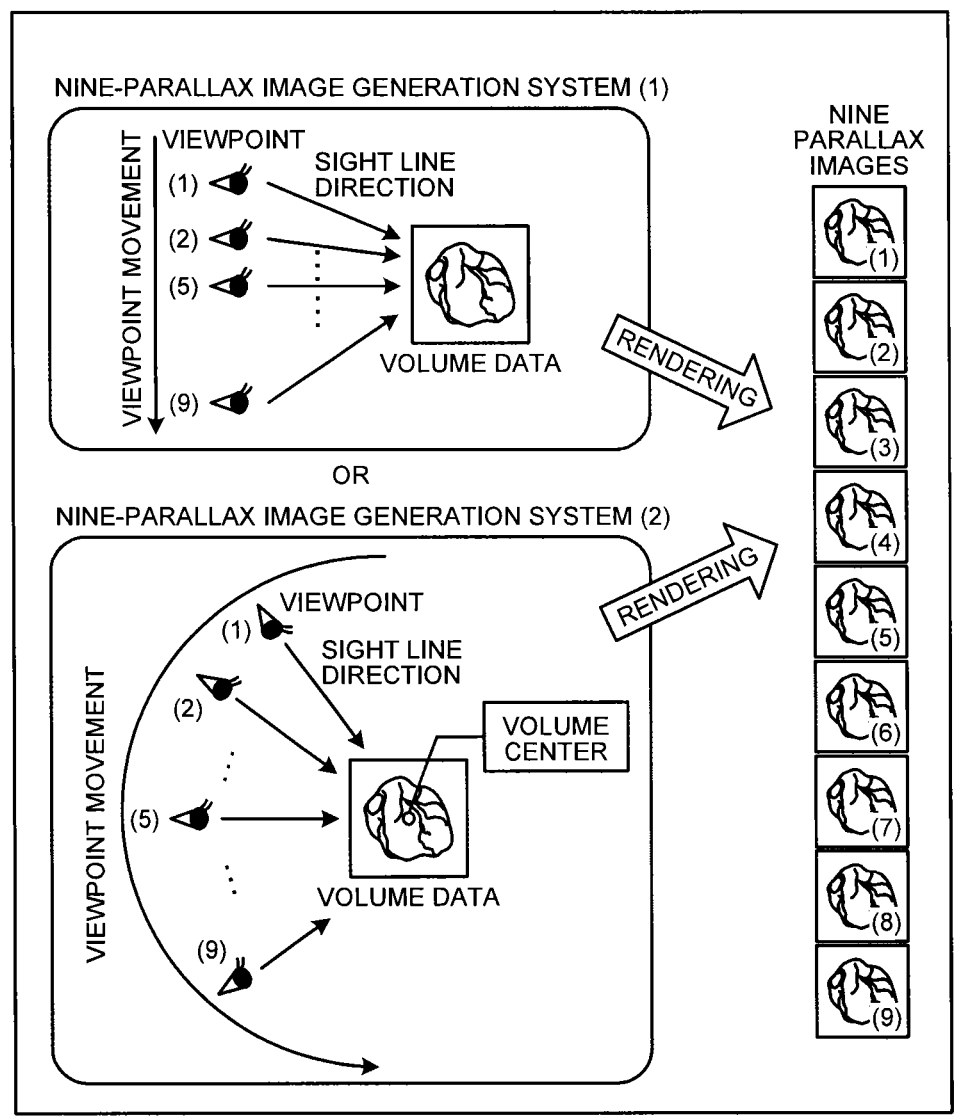
FIG. 6 is a view for explaining an example of volume rendering processing in the first embodiment.

FIG. 6 is a diagram for describing an example of the volume rendering process according to the first embodiment. For example, let us assume that the 3D virtual space rendering unit 1362k receives the parallel projection method as the rendering condition, and further receives a reference point-of-view position (5) and a parallactic angle "1°" as illustrated in a "nine-parallax image generating method (1)" of FIG. 6. In this case, the 3D virtual space rendering unit 1362k shifts the position of a point of view to (1) to (9) in parallel so that the parallactic angle can be changed by "1°", and generates nine parallax images between which the parallactic angle (an angle in a line-of-sight direction) differs from each other by 1° by the parallel projection method. Further, when the parallel projection method is performed, the 3D virtual space rendering unit 1362k sets a light source that emits a parallel beam in a line-of-sight direction from infinity.

Alternatively, the 3D virtual space rendering unit 1362k receives the perspective projection method as the rendering condition, and further receives a reference point-of-view position (5) and a parallactic angle "1°" as illustrated in a "nine-parallax image generating method (2)" of FIG. 6. In this case, the 3D virtual space rendering unit 1362k rotationally moves the position of a point of view to (1) to (9) so that the parallactic angle can be changed by "1°", centering on the center (gravity center) of volume data, and generates nine parallax images between which the parallactic angle differs from each other by 1° by the perspective projection method. Further, when the perspective projection method is performed, the 3D virtual space rendering unit 1362k sets a point light source or a surface light source, which three-dimensionally emits light in a radial manner centering on a line-of-sight direction, at each point of view. Further, when the perspective projection method is performed, the points of view (1) to (9) may be parallel-shifted according to the rendering condition.

Further, the 3D virtual space rendering unit 1362k may perform the volume rendering process using the parallel projection method and the perspective projection method together by setting a light source that two-dimensionally emits light in a radial manner centering on the line-of-sight direction on a longitudinal direction of a volume rendering image to display, and emits a parallel beam in the line-of-sight direction from infinity on a transverse direction of a volume rendering image to display.

The nine parallax images generated in the above-described way configure a parallax image group. In the first embodiment, for example, the nine parallax images are converted into interim images arranged in a predetermined format (for example, a lattice form) by the control unit 135, and then output to the display unit 132 serving as the stereoscopic display monitor. At this time, the operator of the workstation 130 can perform an operation of generating a parallax image group while checking a stereoscopically viewable medical image displayed on the stereoscopic display monitor.

The example of FIG. 6 has been described in connection with the case in which the projection method, the reference point-of-view position, and the parallactic angle are received as the rendering condition. However, similarly even when any other condition is received as the rendering condition, the 3D virtual space rendering unit 1362k generates the parallax image group while reflecting each rendering condition.

Further, the 3D virtual space rendering unit 1362k further has a function of performing a Multi Planer Reconstruction (MPR) technique as well as the volume rendering and reconstructing an MPR image from volume data. The 3D virtual space rendering unit 1362k further has a function of performing a "curved MPR" and a function of performing "intensity projection."

Subsequently, the parallax image group which the 3D image processing unit 1362 has generated based on the volume data is regarded as an underlay. Then, an overlay in which a variety of information (a scale, a patient name, an inspection item, and the like) is represented is superimposed on the underlay, so that a 2D output image is generated. The 2D image processing unit 1363 is a processing unit that performs image processing on the overlay and the underlay and generates a 2D output image, and includes a 2D object rendering unit 1363a, a 2D geometric transform processing unit 1363b, and a brightness adjusting unit 1363c as illustrated in FIG. 5. For example, in order to reduce a load required in a process of generating a 2D output image, the 2D image processing unit 1363 generates nine 2D output images by superimposing one overlay on each of nine parallax images (underlays). In the following, an underlay on which an overlay is superimposed may be referred to simply as a "parallax image."

The 2D object rendering unit 1363a is a processing unit that renders a variety of information represented on the overlay. The 2D geometric transform processing unit 1363b is a processing unit that parallel-shifts or rotationally moves the position of a variety of information represented on the overlay, or enlarges or reduces a variety of information represented on the overlay.

The brightness adjusting unit 1363c is a processing unit that performs a brightness converting process. For example, the brightness adjusting unit 1363c adjusts brightness of the overlay and the underlay according to an image processing parameter such as gradation of a stereoscopic display monitor of an output destination, a window width (WW), or a window level (WL).

For example, the control unit 135 stores the 2D output image generated as described above in the storage unit 134, and then transmits the 2D output image to the image storage device 120 through the communication unit 133. Then, for example, the terminal device 140 acquires the 2D output image from the image storage device 120, converts the 2D output image into an interim image arranged in a predetermined format (for example, a lattice form), and displays the interim image on the stereoscopic display monitor. Further, for example, the control unit 135 stores the 2D output image in the storage unit 134, then transmits the 2D output image to the image storage device 120 through the communication unit 133, and transmits the 2D output image to the terminal device 140. Then, the terminal device 140 converts the 2D output image transmitted from the workstation 130 into the interim image arranged in a predetermined format (for example, a lattice form), and causes the interim image to be displayed on the stereoscopic display monitor. Through this operation, a doctor or a laboratory technician who uses the terminal device 140 can view a stereoscopically viewable medical image in a state in which a variety of information (a scale, a patient name, an inspection item, and the like) is represented.

As described above, the stereoscopic display monitor in the first embodiment displays a parallax image group so as to provide a stereoscopic image that can be viewed stereoscopically by an observer. For example, the stereoscopic display monitor displays an organ or the like of a subject as a stereoscopic image. With this, an observer who observes the stereoscopic display monitor can visually recognize the organ or the like of the subject stereoscopically. As a parallax angle between parallax images constituting a parallax image group is larger, a stereoscopic effect of the stereoscopic image is increased. For example, when an operation of changing a parallax angle has been performed by an observer, the terminal device 140 acquires a parallax image group corresponding to the parallax angle from the image storage device 120, and displays the acquired parallax image group on the stereoscopic display monitor. With this, the observer can observe a stereoscopic image of which stereoscopic effect has been changed.

However, if the parallax angle of the parallax image group is larger than a predetermined value, a stereoscopic image on a predetermined region is displayed as a stereoscopic image but the stereoscopic image within a region other than the predetermined region is displayed as a rough image (so-called dimmed image) having no stereoscopic effect in some cases. To be more specific, as described with reference to FIG. 6, the rendering processor 136 of the workstation 130 performs the rendering processing from a plurality of viewpoint positions and sight line directions from the plurality of viewpoint positions intersect with one another at a predetermined position on volume data. The intersection of the sight line directions serves as a focus of a parallax image group generated by performing volume rendering from each of the sight line directions. In a stereoscopic image that is displayed on the stereoscopic display monitor, an undimmed image is displayed within the predetermined region of which the center is the focus of the parallax image group, but a dimmed image is displayed within a region distanced from the focus beyond the predetermined value in some cases.

Figure 7:
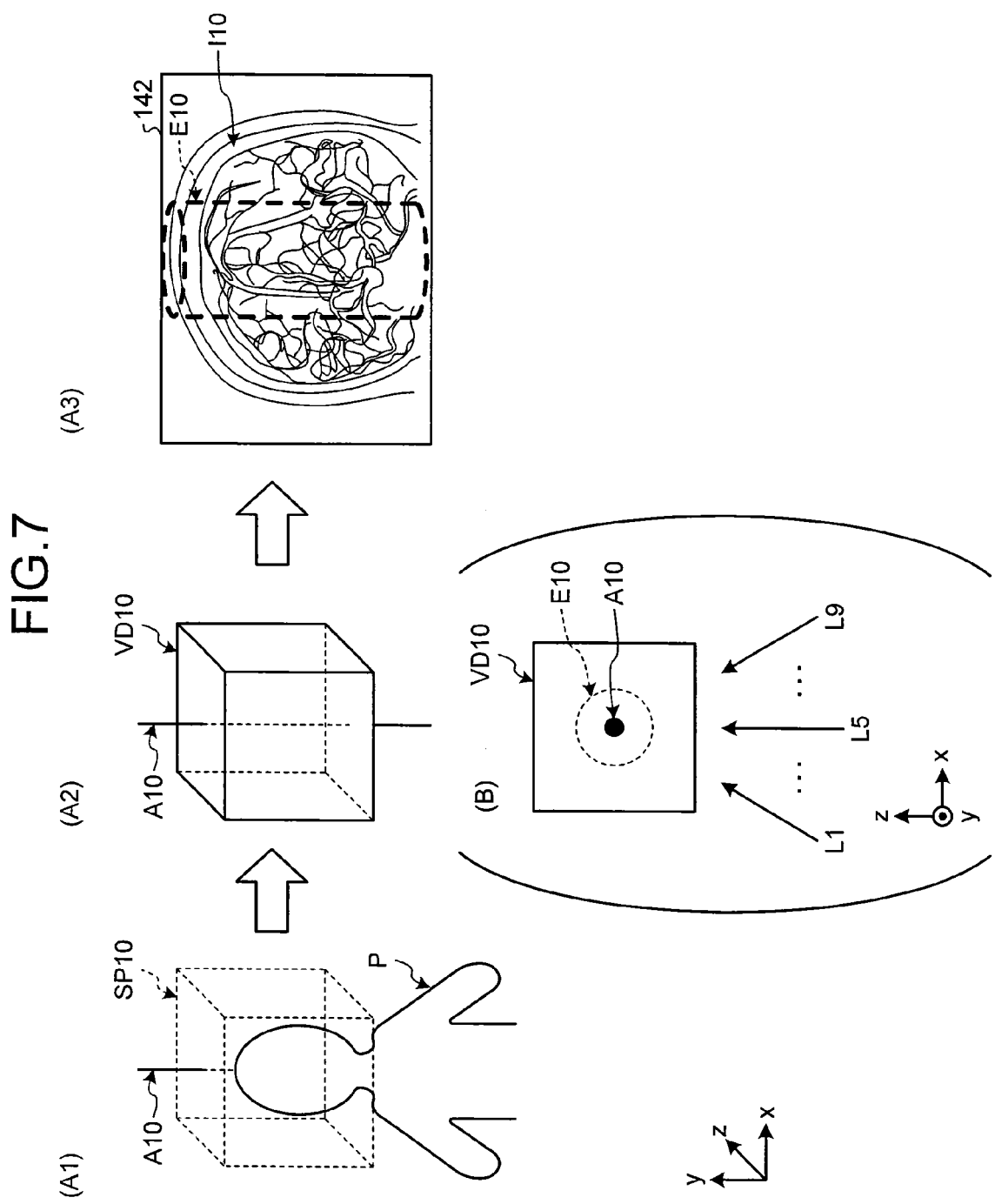
FIG. 7 is a view illustrating an example of a stereoscopic image that is displayed on the stereoscopic display monitor.

Such a focus is described with reference to FIG. 7 using a case in which a rendering condition is a perspective projecting method as an example. FIG. 7 is a view illustrating an example of a stereoscopic image that is displayed on the stereoscopic display monitor. Hereinafter, an example in which the workstation 130 performs rendering processing on volume data generated by the medical image diagnostic device 110 so as to generate a parallax image group, and the terminal device 140 displays the parallax image group on the stereoscopic display monitor 142 thereof is described.

In an example as illustrated in FIG. 7(A1), a predetermined shooting unit that the medical image diagnostic device 110 has shoots a subject P by moving around a head of the subject P about a predetermined straight line A10 as the rotation axis. For example, when the medical image diagnostic device 110 is an X-ray CT device, an annular frame on which an X-ray tube and an X-ray detector are arranged to be opposed to each other moves around the subject P so as to shoot the head of the subject P. Furthermore, in the example as illustrated in FIG. 7(A1), the medical image diagnostic device 110 sets a real space SP10 in which the subject P is present as a shooting target and generates volume data VD10 corresponding to the real space SP10 as illustrated in FIG. 7(A2).

Subsequently, the rendering processor 136 of the workstation 130 performs rendering processing from a plurality of viewpoint positions on the volume data VD10 generated by the medical image diagnostic device 110 so as to generate a parallax image group. To be more specific, the rendering processor 136 performs volume rendering processing while rotating the volume data VD10 based on a movement amount (rotational movement amount) determined by the above-described rotation processor 1362d to change a viewpoint position.

When the rendering condition is the perspective projecting method, the rotation axis when the volume data is rotated is, in general, identical to the rotation axis A10 about which the shooting unit of the medical image diagnostic device 110 moves around the subject P. Furthermore, the rotation axis is an axis passing through the gravity center of the volume data VD10. Accordingly, the rendering processor 136 performs the volume rendering processing while rotating the volume data VD10 about the rotation axis A10 to change the viewpoint position. In other words, the rendering processor 136 moves the viewpoint position on a circular arc about the rotation axis A10 so as to perform the volume rendering processing.

Description is made more in detail with reference to FIG. 7(B). FIG. 7(B) is a view illustrating the volume data VD10 when seen from the above (y direction perpendicular to an xz plane). In FIG. 7(B), an image on which the viewpoint position moves on the circular arc is illustrated. However, the rendering processor 136 may move a viewpoint position by moving the volume data VD10 rotationally. As illustrated in FIG. 7(B), the rendering processor 136 performs the volume rendering processing based on viewpoint positions L1, . . . , L5, . . . , L9 changed on the circular arc about the rotation axis A10. The volume data VD10 seen from the viewpoint positions L1, . . . , L5, . . . , L9 is different from one another. However, the sight line directions from the viewpoint positions to the volume data VD10 direct the same rotation axis A10. That is to say, in the example as illustrated in FIG. 7, a focus at the time of the rendering processing corresponds to the rotation axis A10. In other words, a focus of the parallax image group generated in the above manner corresponds to the rotation axis A10. It is to be noted that the "focus" in this example corresponds to a rotation axis, that is, a "line".

Then, the parallax image group generated by the rendering processor 136 is displayed on the stereoscopic display monitor 142 as illustrated in FIG. 7(A3). To be more specific, the stereoscopic display monitor 142 displays an image in the head of the subject P as a stereoscopic image I10 that can be viewed stereoscopically. When a parallax angle is larger than a predetermined value, the stereoscopic image I10 is an undimmed stereoscopic image within a focus region E10 that is a region in the vicinity of the focus corresponding to the rotation axis A10, but there arises a risk that the stereoscopic image I10 is dimmed within a region other than the focus region E10.

There may be an observer who displays the stereoscopic image I10 more stereoscopically by making the parallax angle larger and also desires to observe the region other than the focus region E10 in some cases. However, even if such an observer performs an operation of making the parallax angle larger, the stereoscopic display monitor 142 may not be able to display an undimmed stereoscopic image within a region desired by the observer in some cases. Therefore, the observer may not be able to observe the desired region more stereoscopically in some cases.

It is to be noted that in the above-described example as illustrated in FIG. 7, a case in which the rendering condition is the perspective projecting method has been described as an example. However, also in a case in which the rendering condition is a parallel projecting method, an intersection of sight line directions when a parallax image group is generated corresponds to a focus of the parallax image group, and a dimmed stereoscopic image is displayed within a region other than a focus region in the vicinity of the focus in some case in the same manner.

In order to solve the problem, the workstation 130 in the first embodiment makes it possible to display an undimmed stereoscopic image within a region desired by an observer by some processing performed by the controller 135. Hereinafter, the workstation 130 and the like in the first embodiment are described in detail. It is to be noted that hereinafter, an example in which the workstation 130 transmits a parallax image group to the terminal device 140, and the terminal device 140 displays the parallax image group received from the workstation 130 is described. Furthermore, hereinafter, a configuration example of the workstation 130 is described, then, a configuration example of the terminal device 140 is described. Thereafter, examples of processing performed by the workstation 130 and the terminal device 140 are described. Finally, procedures of processing performed by the workstation 130 are described.

Figure 8:
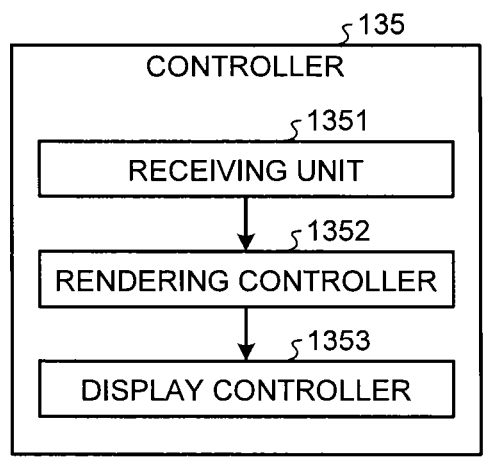
FIG. 8 is a diagram for explaining a configuration example of a controller in the first embodiment.

FIG. 8 is a diagram for explaining a configuration example of the controller 135 in the first embodiment. As illustrated in FIG. 8, the controller 135 in the first embodiment includes a receiving unit 1351, a rendering controller 1352, and a display controller 1353.

The receiving unit 1351 receives a region of interest in a stereoscopic image. To be more specific, the receiving unit 1351 in the first embodiment receives a focus change request to change a focus position on a predetermined stereoscopic image as a region of interest in the stereoscopic image from the terminal device 140 that displays the stereoscopic image on the stereoscopic display monitor 142. The receiving unit 1351 receives, as information relating to a focus position after changed, coordinates in a three-dimensional virtual space (hereinafter, referred to as "volume data space" in some cases) in which volume data as a generation source of a parallax image group that is displayed on the stereoscopic display monitor 142 is arranged. That is to say, the receiving unit 1351 receives a focus position after changed in the volume data space as the region of interest that is displayed so as to be viewed stereoscopically. It is to be noted that the focus change request transmitted from the terminal device 140 will be described in detail later.

The rendering controller 1352 generates a parallax image group from the volume data in corporation with the rendering processor 136. To be more specific, the rendering controller 1352 in the first embodiment controls the rendering processor 136 so as to generate a parallax image group including an image (focus image) indicating a focus that is an intersection of sight line directions at the time of the rendering processing. With this, the rendering processor 136 generates a parallax images including a focus image such as a straight line and a circular column.

When the receiving unit 1351 has received the focus change request, the rendering controller 1352 in the first embodiment determines the sight line directions at the time of the rendering processing based on a focus position after changed that is included in the focus change request. To be more specific, the rendering controller 1352 determines the sight line directions such that the intersection of the sight line directions is substantially identical to the focus position after changed. Then, the rendering controller 1352 controls the rendering processor 136 so as to perform the rendering processing based on the determined sight line directions. With this, the rendering processor 136 performs the rendering processing from each of the sight line directions determined by the rendering controller 1352 so as to generate a new parallax image group.

The display controller 1353 transmits the parallax image group generated by the rendering processor to the terminal device 140. For example, the display controller 1353 in the first embodiment transmits the parallax image group that has been newly generated by the rendering processor to the terminal device 140 and causes the stereoscopic display monitor 142 of the terminal device 140 to display the parallax image group.

Figure 9:
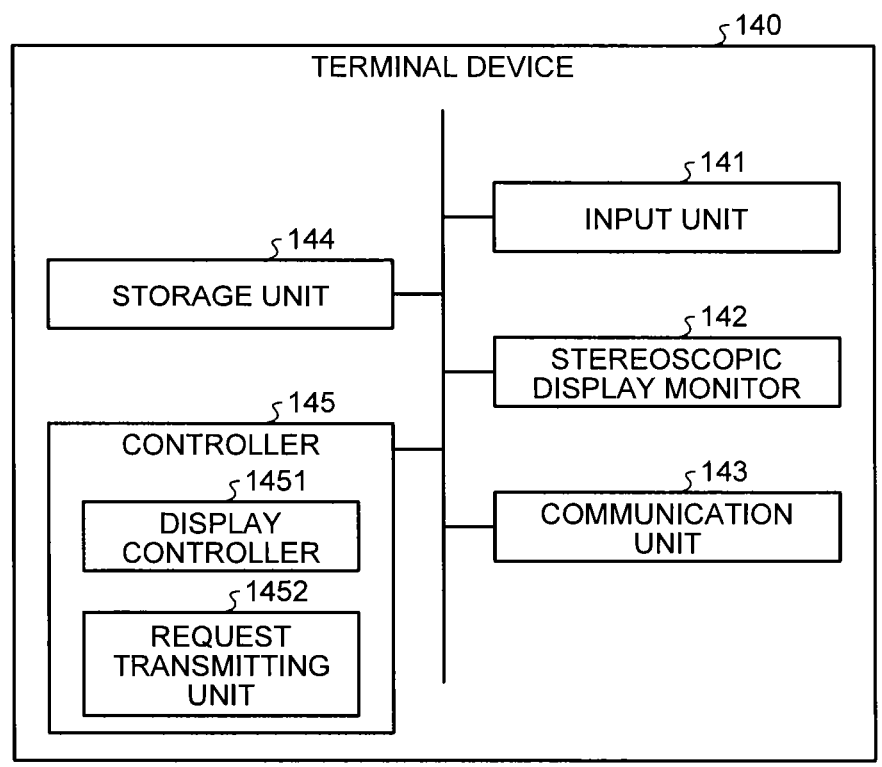
FIG. 9 is a diagram for explaining a configuration example of a terminal device in the first embodiment.

Next, the terminal device 140 in the first embodiment is described with reference to FIG. 9. FIG. 9 is a diagram for explaining a configuration example of the terminal device 140 in the first embodiment. As illustrated in FIG. 9, the terminal device 140 in the first embodiment includes an input unit 141, the stereoscopic display monitor 142, a communication unit 143, a storage unit 144, and a controller 145.

The input unit 141 is a pointing device such as a mouse and a trackball or an information input device such as a keyboard, and receives input of various types of operations on the terminal device 140 from an operator. For example, the input unit 141 receives input of a patient ID, a test ID, a device ID, a series ID, and the like for specifying volume data that is desired to be viewed stereoscopically by the operator, as a stereoscopic view request.

The stereoscopic display monitor 142 is a liquid crystal panel or the like and displays various pieces of information. To be more specific, the stereoscopic display monitor 142 in the first embodiment displays a graphical user interface (GUI) for being received various operations from the operator, a parallax image group, and the like. For example, the stereoscopic display monitor 142 is the stereoscopic display monitor (hereinafter, referred to as two-parallax monitor) as described with reference to FIG. 2A and FIG. 2B, or the stereoscopic display monitor (hereinafter, referred to as nine-parallax monitor) as described with reference to FIG. 6. Hereinafter, a case where the stereoscopic display monitor 142 is the nine-parallax monitor is described.

The communication unit 143 is a network interface card (NIC) or the like and communicates with another device. To be more specific, the communication unit 143 in the first embodiment transmits a stereoscopic view request received by the input unit 141 to the workstation 130. Furthermore, the communication unit 143 in the first embodiment receives a parallax image group transmitted from the workstation 130 in accordance with the stereoscopic view request.

The storage unit 144 is a hard disk, a semiconductor memory element, or the like, and stores therein various pieces of information. To be more specific, the storage unit 144 in the first embodiment stores therein the parallax image group acquired from the workstation 130 through the communication unit 143. Furthermore, the storage unit 144 also stores therein accompanying information (the number of parallaxes, resolution, and the like) of the parallax image group acquired from the workstation 130 through the communication unit 143.

The controller 145 is an electronic circuit such as a CPU, an MPU and a GPU, or an integrated circuit such as an ASIC and an FPGA, and controls the terminal device 140 entirely. For example, the controller 145 controls transmission and reception of a stereoscopic view request and a parallax image group that are performed between the workstation 130 and the terminal device 140 through the communication unit 143. Furthermore, for example, the controller 145 controls storage of the parallax image group in the storage unit 144, and reading of the parallax image group from the storage unit 144.

The controller 145 includes a display controller 1451 and a request transmitting unit 1452 as illustrated in FIG. 9. The display controller 1451 displays a parallax image group received from the workstation 130 on the stereoscopic display monitor 142. With this, the parallax image group is displayed on the stereoscopic display monitor 142 and an observer of the stereoscopic display monitor 142 can observe a stereoscopic image that can be viewed stereoscopically.

The request transmitting unit 1452 transmits a focus change request to change a focus position on a stereoscopic image that is displayed on the stereoscopic display monitor 142 to the workstation 130. To be more specific, when an operation of changing a focus position has been performed by an observer using the input unit 141, the request transmitting unit 1452 transmits the focus change request including a focus position after changed to the workstation 130.

In the first embodiment, it is assumed that an observer specifies a focus position on a stereoscopic image that is displayed on the stereoscopic display monitor 142 by the input unit 141 that is a pointing device or the like. For example, an observer moves a focus image that is displayed as a stereoscopic image using the input unit 141 that is a pointing device or the like so as to set a new focus position.

That is to say, change of a focus position is performed in a three-dimensional space (hereinafter, referred to as "stereoscopic image space" in some cases) in which a stereoscopic image is displayed. In this case, the request transmitting unit 1452 acquires a position (coordinates) in the volume data space that corresponds to the focus position in the stereoscopic image space, and transmits a focus change request including the acquired position (coordinates) in the volume data space to the workstation 130.

Figure 10:
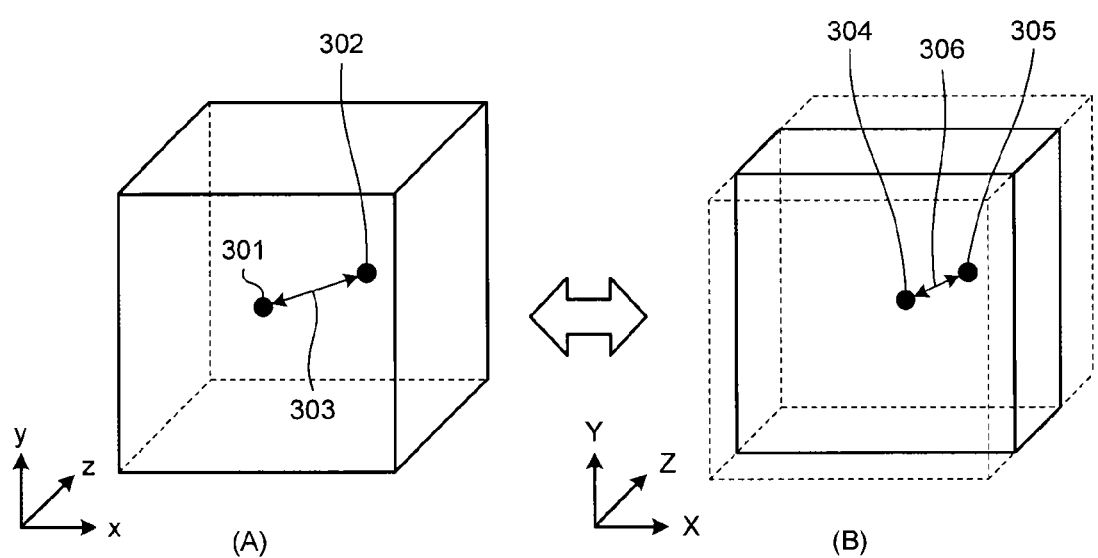
FIG. 10 is a view illustrating an example of a correspondence relationship between a stereoscopic image space and a volume data space.

A correspondence relationship between the stereoscopic image space and the volume data space is described with reference to FIG. 10. FIG. 10 is a view illustrating an example of the correspondence relationship between the stereoscopic image space and the volume data space. FIG. 10(A) illustrates volume data, and FIG. 10(B) illustrates a stereoscopic image that is displayed on the stereoscopic display monitor 142. The coordinate 301, the coordinate 302, and the distance 303 in FIG. 10(A) correspond to the coordinate 304, the coordinate 305, and the distance 306 in FIG. 10(B), respectively.

As illustrated in FIG. 10, coordinate systems of the volume data space in which the volume data is arranged and the stereoscopic image space in which the stereoscopic image is displayed are different from each other. To be more specific, the stereoscopic image as illustrated in FIG. 10(B) is narrower in the depth direction (z direction) in comparison with the volume data as illustrated in FIG. 10(A). In other words, in the stereoscopic image as illustrated in FIG. 10(B), a component of the volume data as illustrated in FIG. 10(A) in the depth direction is compressed to be displayed. In this case, as illustrated in FIG. 10(B), the distance 306 between the coordinate 304 and the coordinate 305 is shorter than the distance 303 between the coordinate 301 and the coordinate 302 as illustrated in FIG. 10(A) by a compressed amount.

Such a correspondence relationship between the coordinates in the stereoscopic image space and the coordinates in the volume data space is determined uniquely with a scale and a view angle of the stereoscopic image, a sight line direction (sight line direction at the time of the rendering or sight line direction at the time of observation of the stereoscopic image), and the like. The correspondence relationship can be expressed in a form of Equation 1 below, for example.

$$(x1, y1, z1) = F(x2, y2, z2) \qquad \text{Equation 1}$$

In Equation 1, each of "x2", "y2", and "z2" indicates a coordinate in the stereoscopic image space. Each of "x1", "y1", and "z1" indicates a coordinate in the volume data space. Furthermore, the function "F" is a function that is determined uniquely with the scale and the view angle of the stereoscopic image, the sight line direction, and the like. That is to say, the request transmitting unit 1452 can acquire the correspondence relationship between the coordinates in the stereoscopic image space and the coordinates in the volume data space using Equation 1. It is to be noted that the function "F" is generated by the request transmitting unit 1452 every time any of the scale and the view angle of the stereoscopic image, the sight line direction (sight line direction at the time of the rendering or sight line direction at the time of observation of the stereoscopic image), and the like is changed. For example, affine conversion as indicated in Equation 2 is used as a function "F" of converting rotation, parallel movement, enlargement, and contraction.

$$x1 = a*x2 + b*y2 + c*z3 + d$$

$$y1 = e*x2 + f*y2 + g*z3 + h$$

$$z1 = i*x2 + j*y2 + k*z3 + l$$

Equation 2

($a$ to $l$ are conversion coefficients)

When an operation of specifying a focus position in the stereoscopic image space has been performed, the request transmitting unit 1452 acquires coordinates in the volume data space that correspond to the specified focus position (coordinates) in the stereoscopic image space based on the function "F". Then, the request transmitting unit 1452 sets the acquired coordinates in the volume data space to coordinates of the focus position after changed. Thereafter, the request transmitting unit 1452 transmits the focus change request including the coordinates of the focus position after changed to the workstation 130.

In the above description, an example in which the request transmitting unit 1452 acquires coordinates in the volume data space based on the function "F" has been described. However, it is not limited thereto. For example, the request transmitting unit 1452 may acquire coordinates in the volume data space that correspond to the coordinates in the stereoscopic image space in the following manner. That is, the terminal device 140 has a coordinate table in which coordinates in the stereoscopic image space and coordinates in the volume data space are made to correspond to each other, and the request transmitting unit 1452 searches the coordinate table by using the coordinates in the stereoscopic image space as a search key.

Figure 11:
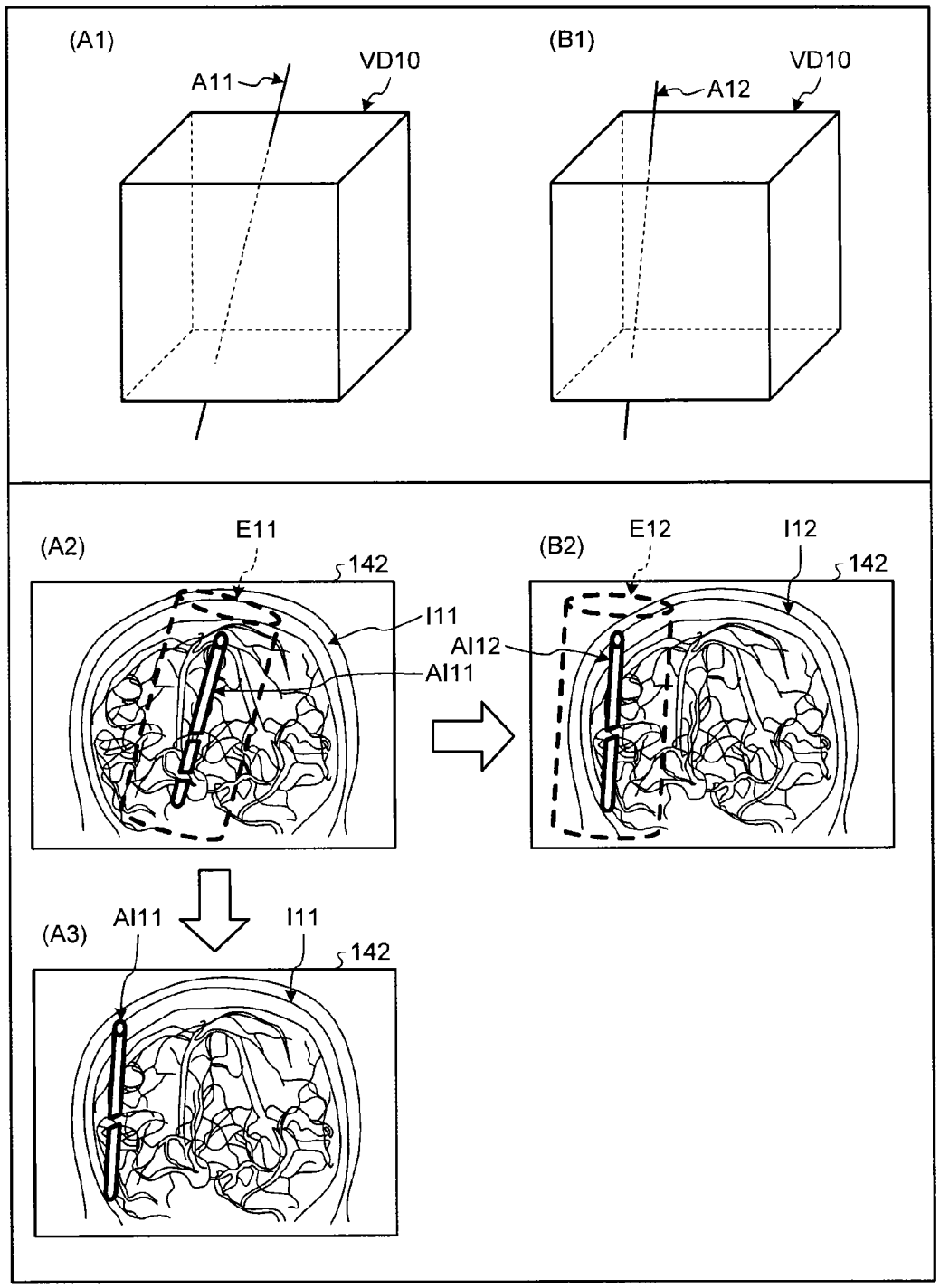
FIG. 11 is a view for explaining an example of processing performed by the workstation and the terminal device in the first embodiment.

Next, an example of processing performed by the workstation 130 and the terminal device 140 in the first embodiment are described with reference to FIG. 11. FIG. 11 is a view for explaining an example of processing performed by the workstation 130 and the terminal device 140 in the first embodiment. FIGS. 11(A1) and 11(B1) illustrate the same volume data VD10, and FIGS. 11(A2), 11(A3) and 11(B2) illustrate a stereoscopic image that is displayed on the stereoscopic display monitor 142 of the terminal device 140.

First, the rendering processor 136 of the workstation 130 is controlled by the rendering controller 1352 so as to perform the rendering processing on the volume data VD10. In this case, as illustrated in FIG. 11(A1), the rendering processor 136 performs the rendering processing on the volume data VD10 under a rendering condition that an intersection of sight line directions corresponds to a straight line A11 so as to generate a parallax image group corresponding to a plurality of viewpoint positions. For example, when the rendering condition is a perspective projecting method, the rendering processor 136 rotates the volume data VD10 about the straight line A11 as the rotation axis so as to generate a parallax image group corresponding to a plurality of viewpoint positions. Furthermore, the rendering processor 136 superimposes a focus image (overlay) indicating the straight line A11 on the parallax image group (underlay). It is to be noted that the rendering processor 136 may perform the rendering processing after data of the focus image has been reflected on the volume data VD10 so as to generate a parallax image group on which the focus image has been reflected.

Then, the workstation 130 transmits the parallax image group that has been generated in this manner to the terminal device 140. With this, as illustrated in FIG. 11(A2), the terminal device 140 displays a stereoscopic image I11 and a focus image AI11 on the stereoscopic display monitor 142. This enables an observer to grasp a focus position in the stereoscopic image I11 based on the focus image AI11.

In the example as illustrated in FIG. 11(A2), it is assumed that an undimmed stereoscopic image is displayed within a focus region E11 in the stereoscopic image I11 but a dimmed stereoscopic image is displayed within a region other than the focus region E11. Furthermore, it is assumed that the focus image AI11 is moved by an observer using the input unit 141, as illustrated in FIG. 11(A3). In such a case, the request transmitting unit 1452 of the terminal device 140 acquires coordinates in the volume data space that correspond to coordinates of the focus image AI11 in the stereoscopic image space as illustrated in FIG. 11(A3) using the above-described function "F". Then, the request transmitting unit 1452 transmits a focus change request including the acquired coordinates in the volume data space to the workstation 130.

Subsequently, when the rendering controller 1352 of the workstation 130 has received the focus change request from the terminal device 140, the rendering controller 1352 controls the rendering processor 136 so as to perform the rendering processing under a rendering condition that a focus position (coordinates in the volume data space) included in the focus change request is identical to an intersection of sight line directions. With this, the rendering processor 136 performs the rendering processing on the volume data VD10 under the rendering condition that the intersection of the sight line directions is a straight line A12 as illustrated in FIG. 11(B1) so as to generate a parallax image group newly. Then, the display controller 1353 of the workstation 130 transmits the new parallax image group that has been generated in this manner to the terminal device 140.

Then, as illustrated in FIG. 11(B2), the terminal device 140 displays a stereoscopic image I12 and a focus image AI12 on the stereoscopic display monitor 142. With this, an undimmed stereoscopic image is displayed on a focus region E12 in the stereoscopic image I12. Therefore, the observer can observe an undimmed stereoscopic image on a desired region.

Figure 12:
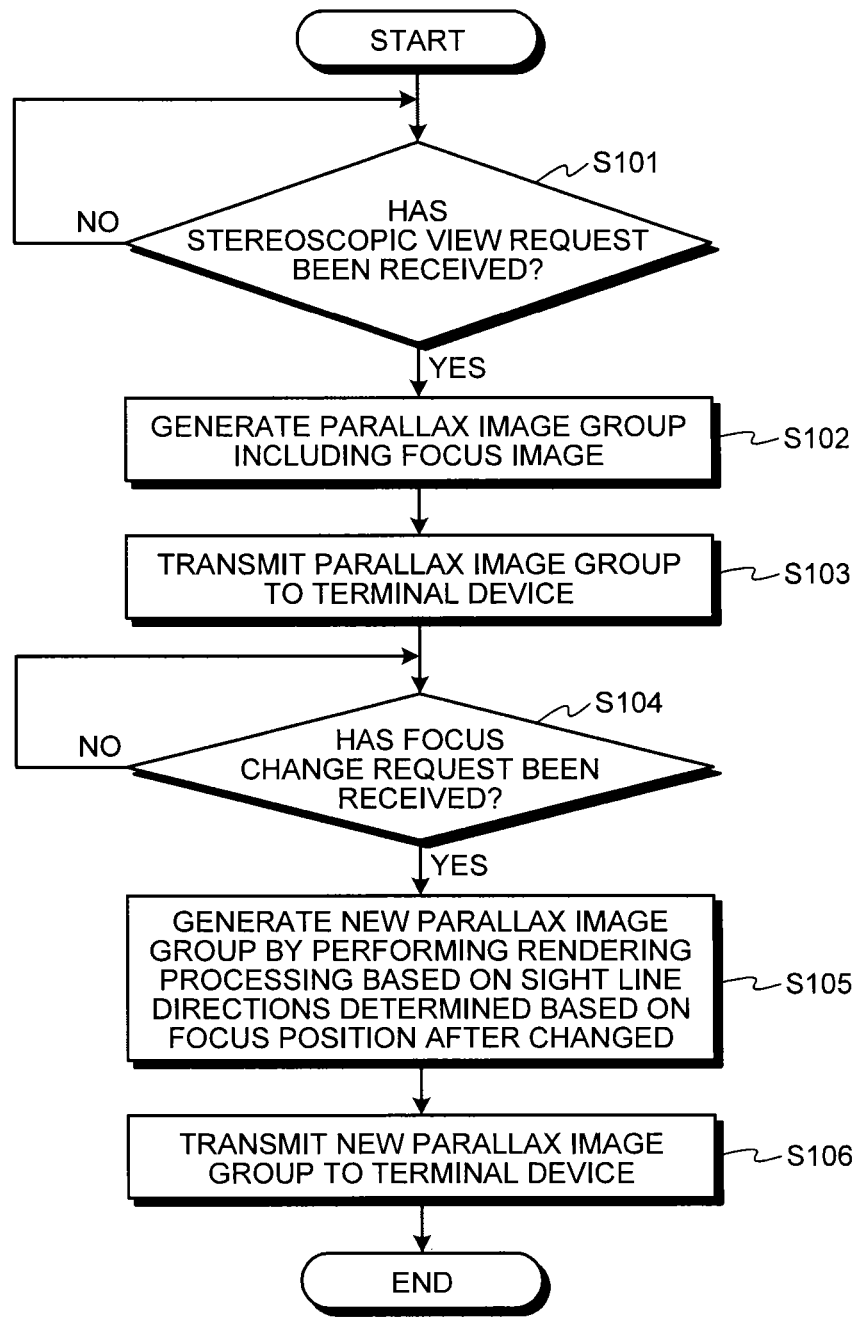
FIG. 12 is a flowchart illustrating an example of a processing flow by the workstation in the first embodiment.

Next, an example of a processing flow by the workstation 130 in the first embodiment is described with reference to FIG. 12. FIG. 12 is a flowchart illustrating an example of the processing flow by the workstation 130 in the first embodiment.

As illustrated in FIG. 12, the controller 135 of the workstation 130 determines whether a stereoscopic view request has been received from the terminal device 140 (S101). When the stereoscopic view request has not been received (No at S101), the workstation 130 stands by until the stereoscopic view request is received.

On the other hand, when the stereoscopic view request has been received (Yes at S101), the rendering controller 1352 of the workstation 130 controls the rendering processor 136 so as to generate a parallax image group including a focus image (S102).

Then, the display controller 1353 of the workstation 130 transmits the parallax image group generated by the rendering processor 136 to the terminal device 140 (S103). With this, the display controller 1353 causes the stereoscopic display monitor 142 of the terminal device 140 to display a stereoscopic image including a focus image as illustrated in FIG. 11(A2) and the like.

Subsequently, the receiving unit 1351 of the workstation 130 determines whether a focus change request has been received from the terminal device 140 (S104). When the focus change request has not been received (No at S104), the receiving unit 1351 stands by until the focus change request is received.

On the other hand, when the receiving unit 1351 has received the focus change request (Yes at S104), the receiving unit 1351 outputs information (coordinates in the volume data space) relating to a focus position after changed that is included in the focus change request to the rendering controller 1352.

The rendering controller 1352 determines sight line directions that are a rendering condition based on the focus position input from the receiving unit 1351, and controls the rendering processor 136 so as to perform the rendering processing under the determined rendering condition. With this, the rendering processor 136 performs the rendering processing under the rendering condition and generates a new parallax image group (S105).

Then, the display controller 1353 transmits the parallax image group that has been generated newly by the rendering processor 136 to the terminal device 140 (S106). With this, the display controller 1353 causes the stereoscopic display monitor 142 of the terminal device 140 to display a stereoscopic image on which the focus position has been changed.

As described above, according to the first embodiment, a focus image can be displayed and a new parallax image group can be generated based on a movement operation of the focus image. Therefore, a focus position in the stereoscopic image can be changed.

It is to be noted that the first embodiment is not limited to the above-described embodiment and may be an embodiment in a mode including any of several modifications as will be described below. Hereinafter, modifications of the first embodiment are described.

Specification of Focus Position

In the above-described first embodiment, an example in which a focus position is set by moving a focus image using the input unit 141 such as a pointing device has been described. However, a method of setting a focus position is not limited thereto. For example, the terminal device 140 may specify a predetermined straight line in the stereoscopic image space with a pointing device or the like so as to receive the predetermined straight line as a focus position after changed.

Furthermore, the terminal device 140 may specify a predetermined three-dimensional region in the stereoscopic image space with a pointing device or the like. In such a case, the rendering controller 1352 sets a predetermined straight line included in the specified three-dimensional region as a new focus position.

It is to be noted that in the above example, the three-dimensional region set in the stereoscopic image space may be an arbitrary shape and is a rectangular parallelepiped, or ellipsoid, for example. Furthermore, as the method of setting a three-dimensional region, the following method is exemplified. That is, a pointing device is operated so as to move a cursor that is displayed on the stereoscopic display monitor 142 in a lateral direction and a vertical direction, and the pointing device is operated in a state where a predetermined key is pressed so as to move the cursor in the depth direction.

Change of Parallax Angle

Furthermore, as described above, when a predetermined three-dimensional region is specified in a stereoscopic image space, and a predetermined straight line included in the specified three-dimensional region is set to a focus position after changed, the rendering controller 1352 may change a parallax angle such that an undimmed stereoscopic image is displayed in the three-dimensional region. To be more specific, as the parallax angle of a parallax image group is larger, a region with dim is larger in the stereoscopic image. Then, the rendering controller 1352 may set a predetermined straight line included in the three-dimensional region that has been set by an observer or the like to a new focus position, determine a parallax angle with which an undimmed stereoscopic image is displayed in the three-dimensional region, and control the rendering processor 136 so as to perform the rendering processing based on the determined parallax angle. With this, the terminal device 140 can display an undimmed stereoscopic image in the three-dimensional region that has been set by the observer.

Second Embodiment

In the above-described first embodiment, an example in which a stereoscopic image including a focus image is displayed and a focus position in the stereoscopic image is moved with an operation of moving the focus image has been described. In the second embodiment, an example in which a focus position on a stereoscopic image is moved with movement of a medical device such as a knife is described.

First, a workstation 230 in the second embodiment is described. The workstation 230 corresponds to the workstation 130 as illustrated in FIG. 1. Furthermore, since a configuration of a controller 235 that the workstation 230 in the second embodiment has is the same as that of the configuration example of the controller 135 as illustrated in FIG. 8, the controller 235 is not illustrated. However, the controller 235 in the second embodiment performs processing that is different from that performed by the receiving unit 1351 and the rendering controller 1352 that the controller 135 has. Then, the controller 235 has a receiving unit 2351 instead of the receiving unit 1351 that the controller 135 has, and has a rendering controller 2352 instead of the rendering controller 1352. Hereinafter, these processors are described with reference to FIG. 13.

Figure 13:
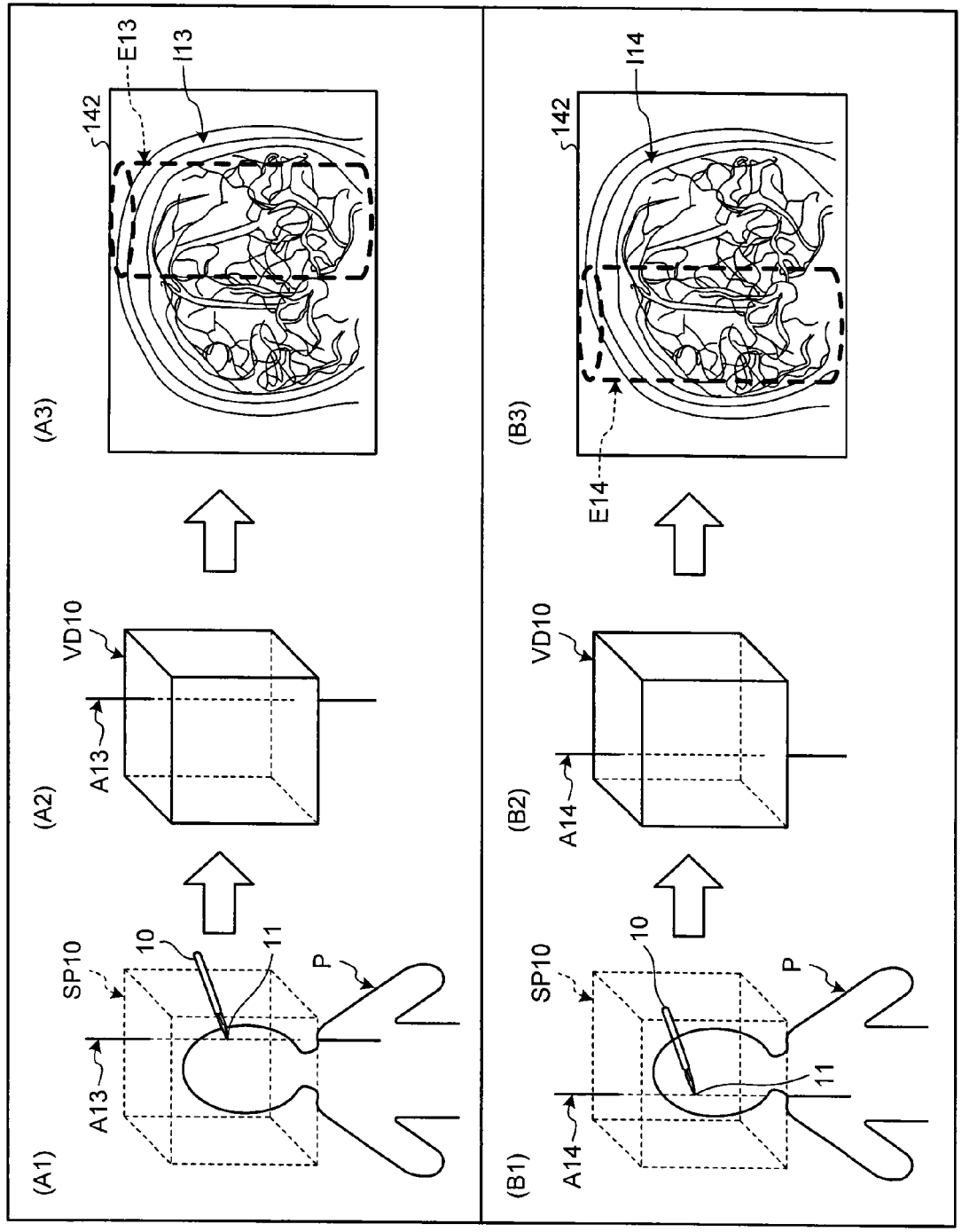
FIG. 13 is a view for explaining processing performed by the controller according to a second embodiment.

FIG. 13 is a views for explaining processing performed by the controller 235 according to the second embodiment. In an example as illustrated in FIG. 13, it is assumed that volume data VD10 is generated previously when a real space SP10 in which a subject P is present has been shot by the medical image diagnostic device 110. Furthermore, it is assumed that a parallax image group that is generated from the volume data VD10 is displayed on the stereoscopic display monitor 142, and a physician or the like performs an operation on the subject P using a medical device 10 while observing the stereoscopic image that is displayed on the stereoscopic display monitor 142.

A position sensor 11 that can acquire a position (coordinates) of a tip of the medical device 10 in the real space SP10 is provided at the tip of the medical device 10. The position sensor 11 transmits the position (coordinates) of the medical device 10 in the real space SP10 to the workstation 230.

Under the configuration, the receiving unit 2351 in the second embodiment receives a position (coordinates) of the medical device 10 in the real space SP10 from the position sensor 11, and outputs the received position to the rendering controller 2352. That is to say, the receiving unit 2351 receives the position of the medical device 10 in the real space SP10 as a region of interest to be displayed so as to be viewed stereoscopically.

Furthermore, the rendering controller 2352 in the second embodiment determines sight line directions as a rendering condition based on the position (coordinates) of the medical device 10 in the real space SP10 that has been input from the receiving unit 2351, and controls the rendering processor 136 so as to perform the rendering processing under the determined rendering condition.

For example, it is assumed that the medical device 10 is located at a position as illustrated in FIG. 13(A1). In such a case, the receiving unit 2351 outputs the position of the medical device 10 that has been received from the position sensor 11 to the rendering controller 2352. The rendering controller 2352 acquires a position in the volume data space that corresponds to the position (coordinates) of the medical device 10 in the real space SP10 that has been input from the receiving unit 2351. It is to be noted that the rendering controller 2352 can acquire a correspondence relationship between a coordinate system of the real space SP10 and a coordinate system of the volume data space based on a generation condition of the volume data VD10. The rendering controller 2352 acquires the generation condition from accompanying information of the volume data VD10 that has been stored in the image storage device 120, for example.

Then, the rendering controller 2352 determines that a straight line in a predetermined direction that passes through the position of the medical device 10 in the volume data VD10 is set to a focus position. The "predetermined direction" may be set previously by an observer such as a physician or may be set fixedly in the image processing system 1. In this example, the rendering controller 2352 determines that a straight line A13 parallel with the vertical direction (y direction) and passing through the position of the medical device 10 is set to a focus position as in an example as illustrated in FIG. 13(A2). Then, the rendering controller 2352 controls the rendering processor 136 so as to perform the rendering processing under the rendering condition that the straight line A13 is set to a focus position.

With this, the rendering processor 136 performs the rendering processing under the rendering condition that an intersection of sight line directions corresponds to the straight line A13 so as to generate a parallax image group. Then, the display controller 1353 transmits the parallax image group that has been generated in this manner to the terminal device 140. As illustrated in FIG. 13(A3), the terminal device 140 displays a stereoscopic image I13 on the stereoscopic display monitor 142. An undimmed stereoscopic image is displayed on a focus region E13 in the stereoscopic image I13. That is to say, an undimmed stereoscopic image is displayed within a region in the vicinity of the position at which the medical device 10 is located on the stereoscopic image I13.

Subsequently, it is assumed that the medical device 10 is moved to a position as illustrated in FIG. 13(B1) by a physician or the like. In such a case, the receiving unit 2351 outputs the position of the medical device 10 that has been received from the position sensor 11 to the rendering controller 2352. The rendering controller 2352 acquires a position (coordinates) in the volume data space that corresponds to the position (coordinates) of the medical device 10 in the real space SP10 that has been input from the receiving unit 2351, and determines that a straight line in a predetermined direction that passes through the acquired position is set to a focus position. In this example, the rendering controller 2352 determines that a straight line A14 is set to a focus position as in an example as illustrated in FIG. 13(B2). Then, the rendering controller 2352 controls the rendering processor 136 so as to perform the rendering processing under a rendering condition that the straight line A14 is set to the focus position.

Thereafter, the display controller 1353 transmits the parallax image group that has been generated in this manner to the terminal device 140. The terminal device 140 displays a stereoscopic image I14 on the stereoscopic display monitor 142 as illustrated in FIG. 13(B3). An undimmed stereoscopic image is displayed on a focus region E14 in the stereoscopic image I14. That is to say, an undimmed stereoscopic image is displayed within a region in the vicinity of the position at which the medical device 10 is located on the stereoscopic image I14.

As described above, in the second embodiment, a focus position on a stereoscopic image is moved with movement of the medical device 10. With this, an observer such as a physician can observe an undimmed stereoscopic image at an operation target site.

Figure 14:
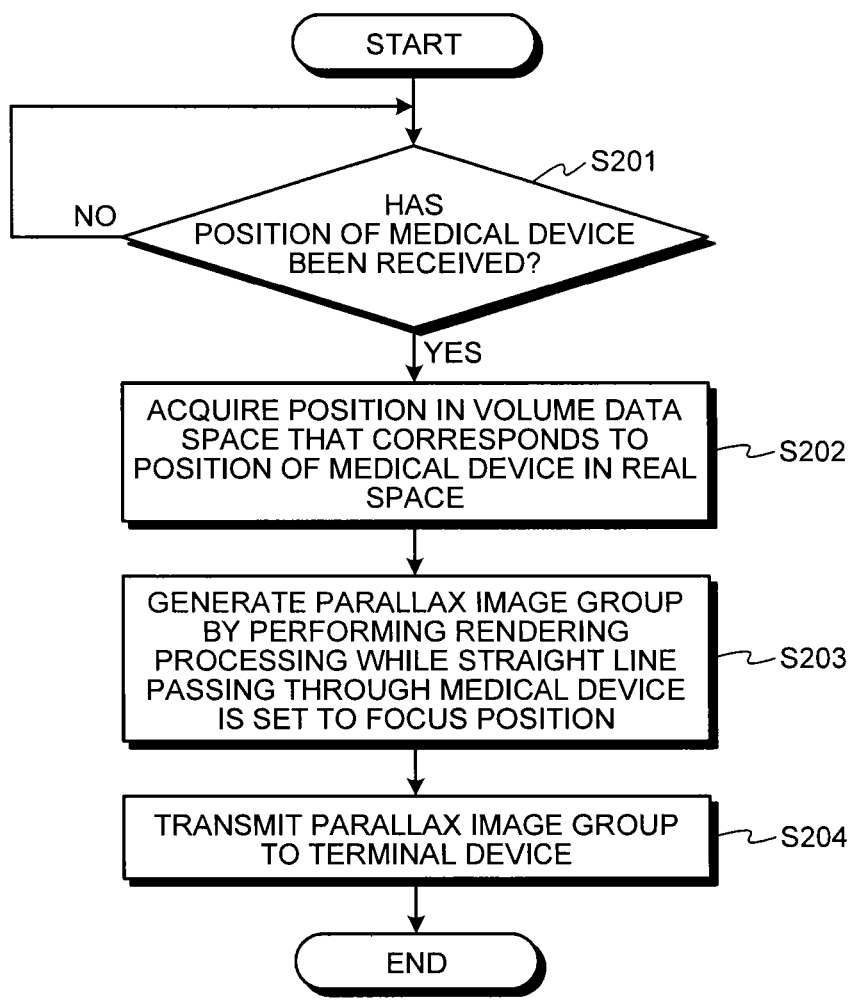
FIG. 14 is a flowchart illustrating an example of a processing flow by the workstation in the second embodiment.

Next, an example of a processing flow by the workstation 230 in the second embodiment is described with reference to FIG. 14. FIG. 14 is a flowchart illustrating an example of the processing flow by the workstation 230 in the second embodiment.

As illustrated in FIG. 14, the receiving unit 2351 of the workstation 230 judges whether a position of the medical device 10 in a real space in which a subject is present has been received from the position sensor 11 included at a tip of the medical device 10 (S201). When the position of the medical device 10 has not been received (No at S201), the receiving unit 2351 stands by until the position of the medical device 10 is received.

On the other hand, when the position of the medical device 10 has been received (Yes at S201), the rendering controller 2352 acquires a position in the volume data space that corresponds to the position of the medical device 10 in the real space SP10 that has been received by the receiving unit 2351 (S202). Then, the rendering controller 2352 controls the rendering processor 136 so as to perform the rendering processing while a straight line in a predetermined direction that passes through the acquired position is set to a focus position. In such a case, the rendering processor 136 performs the rendering processing so as to generate a parallax image group (S203).

Then, the display controller 1353 transmits the parallax image group that has been generated in this manner to the terminal device 140 (S204). With this, the display controller 1353 causes the stereoscopic display monitor 142 of the terminal device 140 to display an undimmed stereoscopic on a focus region in the vicinity of the position at which the medical device 10 is located.

As described above, according to the second embodiment, a focus position in the stereoscopic image is moved with movement of the medical device. Therefore, an undimmed stereoscopic image can be displayed on an operation target site.

It is to be noted that in the above-described second embodiment, the workstation 230 may generate a parallax image group including a focus image in the same manner as the workstation 130. That is to say, the first embodiment and the second embodiment may be combined with each other.

Third Embodiment

In the above-described first and second embodiments, when the workstation 130 or 230 has received information relating to a focus position after changed from the terminal device 140 or the position sensor 11, the workstation 130 or 230 performs rendering processing on volume data based on the information again so as to generate a new parallax image group, and transmits the generated parallax image group to the terminal device. However, the workstation may generate parallax image groups of which focus positions are different from one another previously. In such a case, when the workstation has received information relating to a focus position after changed from the terminal device 140 or the position sensor 11, the workstation transmits a parallax image group corresponding to the focus position after changed to the terminal device 140. In the third embodiment, an example in which parallax image groups of which focus positions are different from one another are generated previously is described.

First, a workstation 330 in the third embodiment is described. The workstation 330 corresponds to the workstation 130 as illustrated in FIG. 1. Furthermore, since a configuration of a controller 335 that the workstation 330 in the third embodiment has is the same as the configuration example of the controller 135 as illustrated in FIG. 8, the controller 335 is not illustrated. However, the controller 335 in the third embodiment performs processing that is different from that performed by the rendering controller 1352 that the controller 135 has. Then, the controller 335 has a rendering controller 3352 instead of the rendering controller 1352 that the controller 135 has. Hereinafter, these processors are described with reference to FIG. 15.

Figure 15:
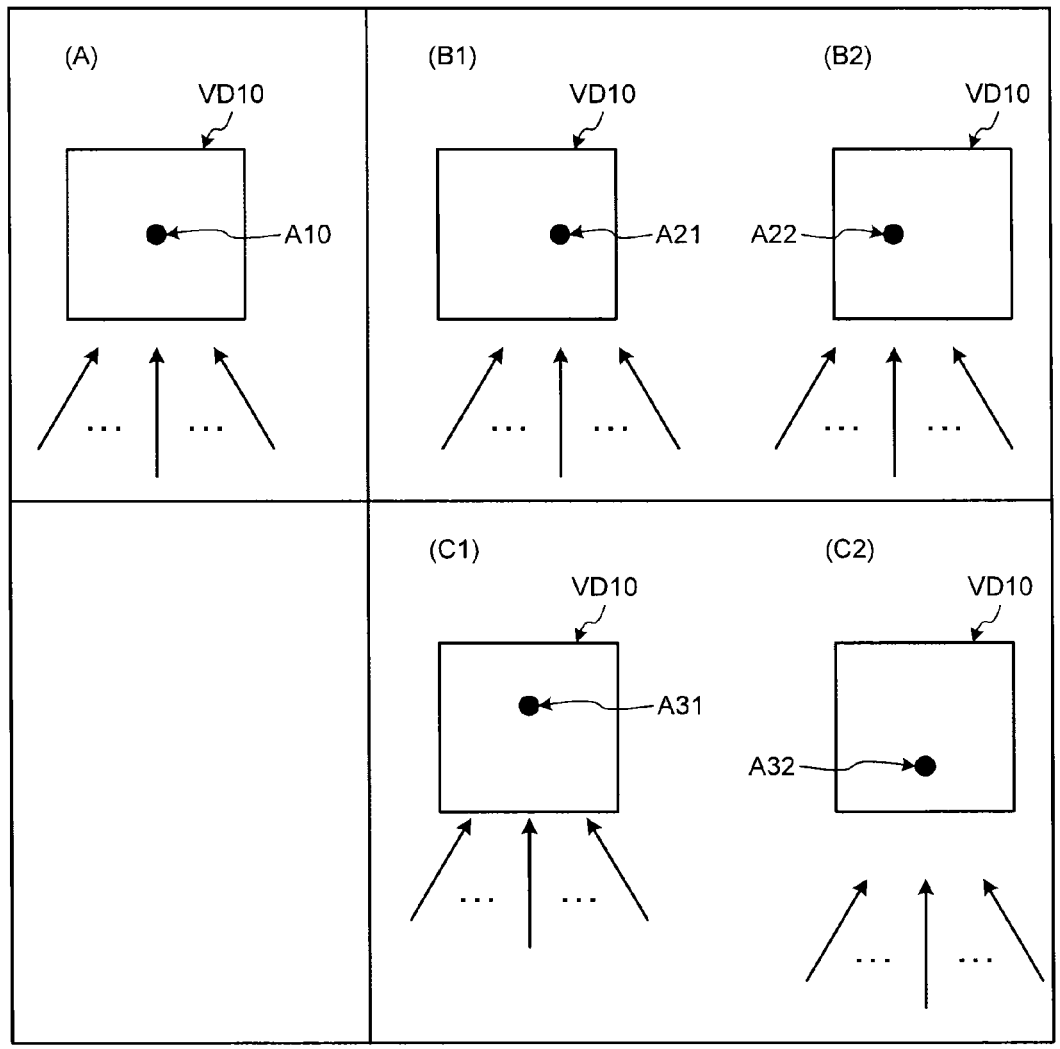
FIG. 15 is a view for explaining processing performed by the controller according to a third embodiment.

FIG. 15 is a view for explaining processing performed by the controller 335 in the third embodiment. It is to be noted that in an example as illustrated in FIG. 15, it is assumed that a rendering condition is a perspective projecting method. Furthermore, FIG. 15 illustrates volume data VD10 when seen from the above (y direction perpendicular to an xy plane). As illustrated in FIG. 15, the rendering controller 3352 in the third embodiment controls the rendering processor 136 so as to perform the rendering processing on the same volume data VD10 based on a plurality of focus positions.

For example, as illustrated in FIG. 15(A), the rendering controller 3352 controls the rendering processor 136 so as to perform the rendering processing under a rendering condition that a center of the volume data VD10 is set to a focus position A10 (straight line A10). With this, the rendering processor 136 generates a parallax image group corresponding to the focus position A10.

Furthermore, as illustrated in FIG. 15(B1), the rendering controller 3352 controls the rendering processor 136 so as to perform the rendering processing while a focus position A21 located at a positive side in an x-axis direction relative to the focus position A10 is set to a rendering condition. With this, the rendering processor 136 generates a parallax image group corresponding to the focus position A21. Furthermore, as illustrated in FIG. 15(B2), the rendering controller 3352 controls the rendering processor 136 so as to perform the rendering processing while a focus position A22 located at a negative side in the x-axis direction relative to the focus position A10 is set to a rendering condition. With this, the rendering processor 136 generates a parallax image group corresponding to the focus position A22.

In the same manner, as illustrated in FIGS. 15(C1) and 15(C2), the rendering controller 3352 controls the rendering processor 136 so as to perform the rendering processing while a focus position A31 located at a positive side in a z-axis direction relative to the focus position A10 and a focus position A32 located at a negative side in the z-axis direction relative to the focus position A10 are set to rendering conditions. Therefore, the rendering processor 136 generates a parallax image group corresponding to the focus position A31 and a parallax image group corresponding to the focus position A32.

The rendering controller 3352 stores a plurality of parallax image groups that have been generated in this manner in the image storage device 120. In this case, the rendering controller 3352 stores each parallax image group in the image storage device 120 so as to correspond to each focus position used at the time of the rendering processing.

Then, as in the above-described first embodiment, when the receiving unit 1351 has received a focus change request, the rendering controller 3352 acquires a parallax image group corresponding to a focus position after changed included in the focus change request from the image storage device 120, and transmits the acquired parallax image group to the terminal device 140. Furthermore, as in the above-described second embodiment, when the receiving unit 2351 has received a position of the medical device 10 in the real space, the rendering controller 3352 acquires a parallax image group corresponding to the position from the image storage device 120, and transmits the acquired parallax image group to the terminal device 140.

As described above, according to the third embodiment, parallax image groups corresponding to a plurality of focus positions are generated previously. Therefore, when a focus position after changed has been received, a stereoscopic image on which a focus position has been changed can be displayed without performing the rendering processing, again.

It is to be noted that in the above-described third embodiment, an example in which the terminal device 140 acquires a parallax image group from the workstation 330 has been described. However, the terminal device 140 may acquire a parallax image group corresponding to a focus position after changed from the image storage device 120.

In addition, in the above-described third embodiment, the workstation 330 may not generate parallax image groups corresponding to all focus positions. For example, the workstation 330 may receive a region on which a focus position is possibly changed from an observer, and generate only parallax image groups corresponding to focus positions included in the region.

Furthermore, the workstation 330 may generate parallax image groups for the entire circumferences by performing the rendering processing from a plurality of viewpoint positions that are arranged at an interval of a predetermined angle (for example, 1 degree) on circular arcs about focus positions as the image groups corresponding to the focus positions in the example as illustrated in FIG. 15. Alternatively, the workstation 330 may generate parallax image groups corresponding to specified viewpoint positions only by performing the rendering processing from viewpoint positions that are arranged on not the entire circumferences but specified positions on the circular arcs in the example as illustrated in FIG. 15. The workstation 330 may receive information relating to a viewpoint position from an observer when the viewpoint position is specified.

Furthermore, in the above-described third embodiment, a case in which the rendering condition is the perspective projecting method has been described as an example. However, the workstation 330 may generate parallax image groups corresponding to a plurality of focus positions in the same manner when the rendering condition is a parallel projecting method.

Fourth Embodiment

In the above-described first and second embodiments, an example in which change of a focus position is received by the terminal device 140 or the position sensor 11 has been described. However, the terminal device 140 may display a cross-sectional image together with a stereoscopic image, and may receive change of a focus position in the cross-sectional image. Furthermore, the terminal device 140 may receive change of a parallax angle or a display region. In the fourth embodiment, an example in which change of a focus position, a parallax angle, or a display region is received on a cross-sectional image is described.

Figure 16:
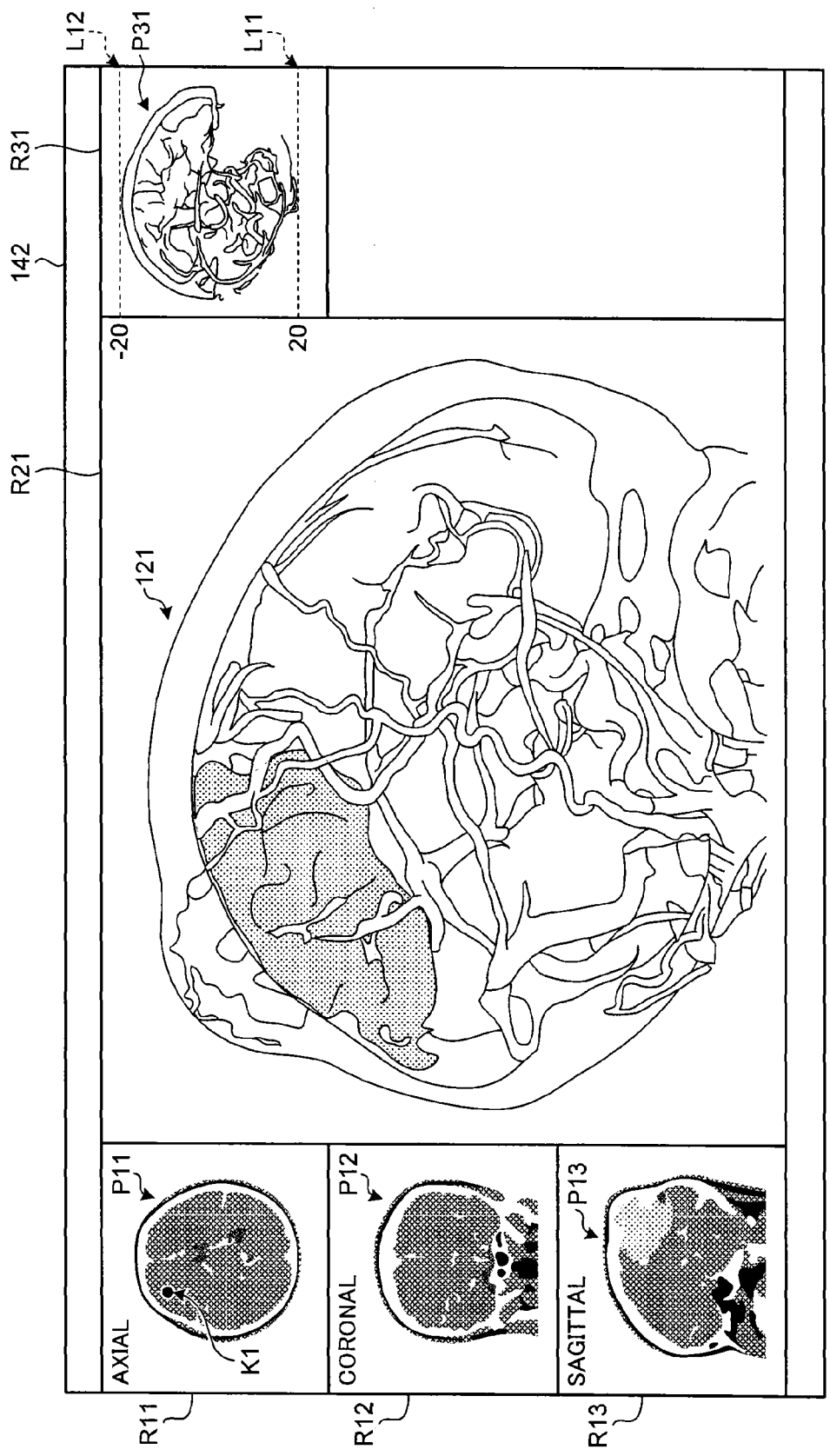
FIG. 16 is a view illustrating a screen example that is displayed on the stereoscopic display monitor according to a fourth embodiment.

First, an example of a screen that is displayed on the stereoscopic display monitor 142 according to the fourth embodiment is described with reference to FIG. 16. As illustrated in FIG. 16, the stereoscopic display monitor 142 displays three perpendicular cross sections (axial surface, coronal surface, and sagittal surface) and a flat image obtained by seeing a stereoscopic image from the above in addition to a stereoscopic image under control by the display controller 1451. To be more specific, in an example as illustrated in FIG. 16, a cross-sectional image P11 of an axial surface is displayed within a region R11, a cross-sectional image P12 of a coronal surface is displayed within a region R12, and a cross-sectional image P13 of a sagittal surface is displayed within a region R13. Furthermore, a stereoscopic image I21 of a cranial bone is displayed within a region R21, and a flat image P31 on which a depth direction of the stereoscopic image I21 is drawn out is displayed within a region R31. It is to be noted that the terminal device 140 can acquire the cross-sectional images P11, P12, and P13 and the flat image P31 from the workstation 130.

Figure 17:
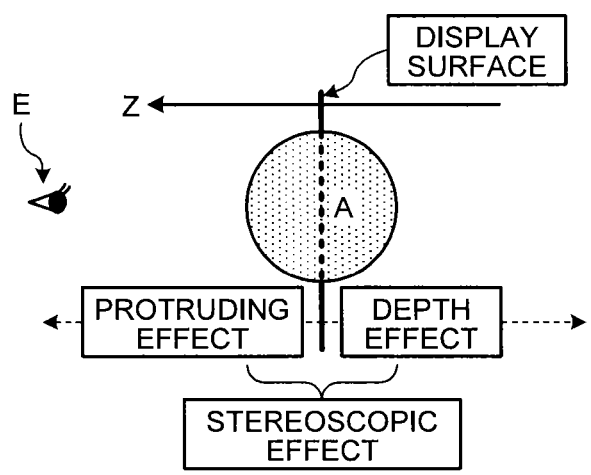
FIG. 17 is a view for explaining the stereoscopic image space.

Straight lines L11 and L12 indicating stereoscopic amounts of the stereoscopic image I21 are displayed on the region R31. This point is described with reference to FIG. 17. FIG. 17 is a view for explaining a stereoscopic image space. As illustrated in FIG. 17, an observer who visually recognizes a parallax image group displayed on the stereoscopic display monitor 142 recognizes a stereoscopic image A in the stereoscopic image space visually stereoscopically. A stereoscopic effect that the observer perceives is classified roughly into a protruding effect and a depth effect as illustrated in FIG. 17. The protruding effect is an effect that the observer perceives such that the stereoscopic image A protrudes in a direction closer to a viewpoint (observer viewpoint E) of the observer from a display surface of the stereoscopic display monitor 142. On the other hand, the depth effect is an effect that the observer perceives such that the stereoscopic image A recedes in a direction farther from the viewpoint (observer viewpoint E) of the observer from the display surface of the stereoscopic display monitor 142.

Hereinafter, the direction closer to the viewpoint of the observer from the display surface of the stereoscopic display monitor 142 is referred to as "protruding direction", and the direction farther from the viewpoint of the observer from the display surface of the stereoscopic display monitor 142 is referred to as "depth direction". To be more specific, the "protruding direction" and the "depth direction" correspond to a direction (z direction in FIG. 17) perpendicular to the display surface of the stereoscopic display monitor 142 in the stereoscopic image space.

On the region R31 as illustrated in FIG. 16, the straight line L11 and "20" (unit: mm) are displayed as a stereoscopic amount of the stereoscopic image I21 in the protruding direction, and the straight line L12 and "−20" (unit: mm) are displayed as a stereoscopic amount of the stereoscopic image I21 in the depth direction.

Figure 18:
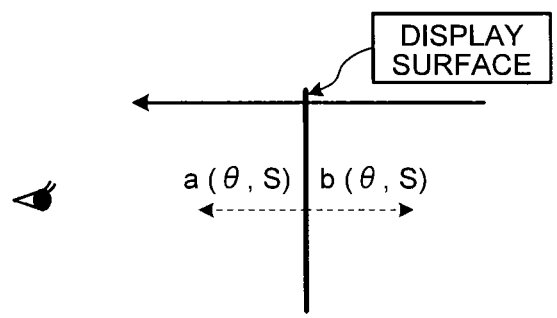
FIG. 18 is a view for explaining a stereoscopic effect of a stereoscopic image.

Such a stereoscopic effect of a stereoscopic image depends on a parallax angle ($\theta$) and a display size (S) in a case of nine-parallax monitor. This point is described with reference to FIG. 18. FIG. 18 is a view for explaining a stereoscopic effect of a stereoscopic image.

As illustrated in FIG. 18, the stereoscopic effect of the stereoscopic image is obtained from parameters "$a(\theta, S)$" and "$b(\theta, S)$" in which the parallax angle ($\theta$) and the display size (S) are variables. To be more specific, the parameter "$a(\theta, S)$" indicates a protruding amount (unit: mm) when the parallax angle is ($\theta$) and the display size of the stereoscopic display monitor 142 is (S). Furthermore, "$b(\theta, S)$" indicates a depth value (unit: mm) when the parallax angle is ($\theta$) and the display size is (S). These parameters "$a(\theta, S)$" and "$b(\theta, S)$" are set previously in accordance with performance of the stereoscopic display monitor 142, and for example, are information set by a manager of the image processing system 1.

A size of the stereoscopic image in the depth direction is limited to a predetermined limit vale based on the performance of the stereoscopic display monitor 142 and the like. Hereinafter, in the stereoscopic image that is displayed on the stereoscopic display monitor 142, a limit value of the size in the direction closer to the viewpoint of the observer from the display surface of the stereoscopic display monitor 142 is referred to as "protrusion limit amount", and a limit value of the size in the direction farther from the viewpoint of the observer from the display surface of the stereoscopic display monitor 142 is referred to as "depth limit amount" in some cases. That is to say, the stereoscopic effect obtained by the above-described "$a(\theta, S)$" and "$b(\theta, S)$" needs to be modified based on the "protrusion limit value" and the "depth limit value" when $a(\theta, S)$" and "$b(\theta, S)$" are beyond the "protrusion limit value" and the "depth limit value", respectively.

As the protrusion limit amount and the depth limit amount are described more in detail, the protrusion limit amount and the depth limit amount are calculated based on the display surface of the stereoscopic display monitor 142, a viewing distance as a distance between the stereoscopic display monitor 142 and an observer who observes the stereoscopic display monitor 142, and hardware performance of the stereoscopic display monitor 142. It is considered that the viewing distance between the stereoscopic display monitor 142 and the observer cannot be obtained unless a position of the observer is identified. However, in general, the stereoscopic display monitor 142 or the like is designed while an observation position of the stereoscopic display monitor 142 is supposed to be a predetermined position. That is to say, the protrusion limit amount and the depth limit amount can be calculated based on a "supposed viewing distance" as the distance between the observation position that has been supposed to be a predetermined position and the display surface of the stereoscopic display monitor 142.

One example of the protrusion limit amount and the depth limit amount is described. For example, the protrusion limit amount is calculated from Formula 1 below and the depth limit amount is calculated from Formula 2 below. It is to be noted that in Formulas 1 and 2 below, a direction closer to a viewpoint of an observer from the display surface is set to a negative side and a direction farther from the viewpoint of the observer from the display surface is set to a positive side while the display surface of the stereoscopic display monitor 142 is set to an origin in the depth direction.

Protrusion limit amount(mm)=−supposed viewing distance/{2×[(supposed viewing distance+gap)/ supposed viewing distance]×(sub-pixel pitch/ gap)×protrusion limit frequency+1}  (1)

Depth limit amount(mm)=supposed viewing distance/{2×[(supposed viewing distance+gap)/ supposed viewing distance]×(sub-pixel pitch/ gap)×protrusion limit frequency−1}  (2)

Figure 19:
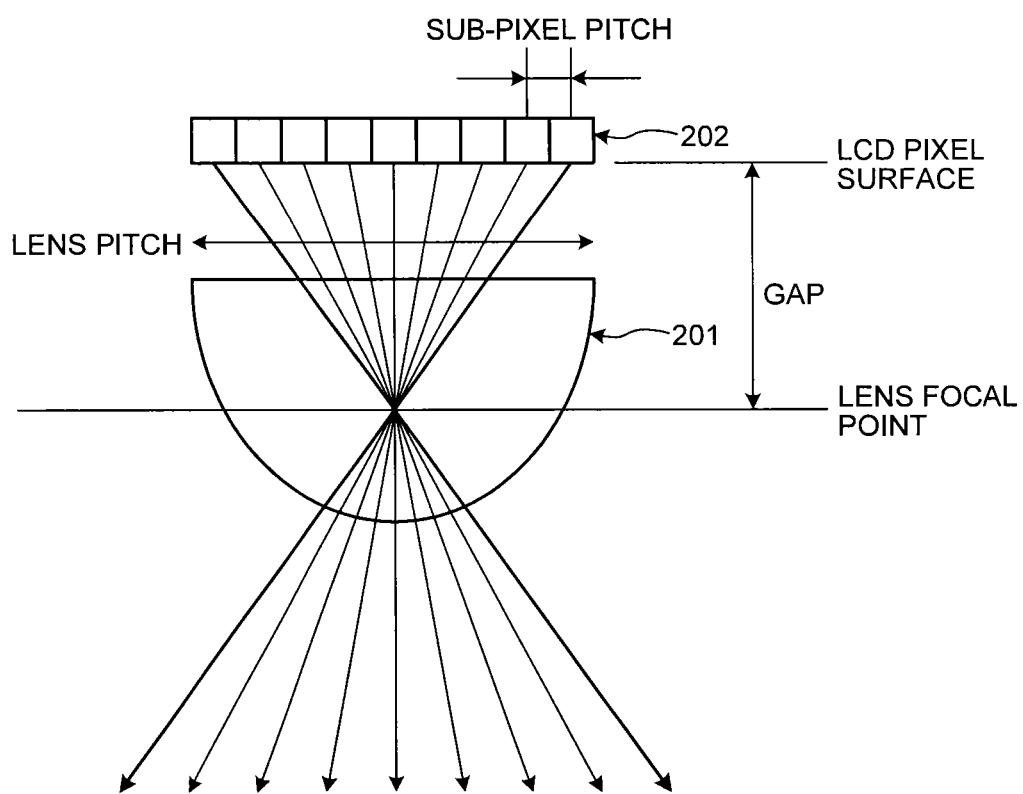
FIG. 19 is a view illustrating the stereoscopic display monitor as illustrated in FIG. 3 when seen from a vertical direction (y-axis direction)

The "gap", the "sub pixel", and the like in Formulas (1) and (2) above are described with reference to FIG. 19. FIG. 19 is a view illustrating the stereoscopic display monitor as illustrated in FIG. 3 when seen from a vertical direction (y-axis direction). As illustrated in FIG. 19, the "gap" indicates a distance between a liquid crystal display (LCD) pixel surface and a focal point of a lenticular lens 201. Furthermore, the "sub pixel pitch" indicates a distance between LCD pixels 202 arranged in the stereoscopic display monitor. In addition, the "lens pitch" indicates a length of the LCD pixels 202 for the number of parallaxes" in the lateral direction and is expressed by "sub-pixel pitch×the number of parallaxes".

Furthermore, a unit of the "protrusion limit frequency" in Formulas (1) and (2) above is "cycles per radian (CPR)" and the "protrusion limit frequency" is expressed by "maximum displayable frequency×N (0<N≤1)". The "maximum displayable frequency" is expressed by "viewing distance/(2× lens pitch)", and indicates a resolution on the display surface of the stereoscopic display monitor 142. As will be described more in detail, the "CPR" indicates density of rays that are permitted by a ray cone spread from eyes of an observer among rays irradiated from the stereoscopic display monitor 142. In a case of the same viewing distance, the "CPR" is higher as the density of the lenticular lens to be arranged is higher and the "CPR" is lower as the density of the lenticular lens to be arranged is lower. In other words, when the density of the lenticular lens to be arranged is the same, the "CPR" is higher as the viewing distance is farther and the "CPR" is lower as the viewing distance is shorter.

The "maximum displayable frequency" is a resolution at which the "CPR" is at the maximum, that is, indicates a resolution on the display surface of the stereoscopic display monitor 142.

In Formulas (1) and (2) above, it is assumed that the viewing distance is "1000 mm", the gap is "0.5 mm", the sub pixel pitch is "0.05 mm", and the protrusion limit frequency is "300 CPR", for example. In such a case, the protrusion limit amount is calculated to be "−16.4 mm" with Formula 1 above, and the depth limit amount is calculated to be "16.9 mm" with Formula 2 above. Note that measured values can be rounded to one decimal place.

A stereoscopic amount is displayed on the region R31 as illustrated in FIG. 16 while the direction closer to the viewpoint of the observer from the display surface is set to a positive side and the direction farther from the viewpoint of the observer from the display surface is set to a negative side unlike the example as illustrated in FIG. 19.

To be more specific, in the example as illustrated in FIG. 16, a protruding amount obtained from the parameter "a(θ, S)" is smaller than a protrusion limit amount obtained by Formula 1 above, the protruding amount obtained from the parameter "a(θ, S)" is displayed on the region R31 as a stereoscopic effect in the direction closer to the viewpoint of the observer from the display surface. On the other hand, when the protruding amount obtained from the parameter "a(θ, S)" is larger than the protrusion limit amount, the protrusion limit amount is displayed on the region R31 as the stereoscopic effect in the direction closer to the viewpoint of the observer from the display surface.

Furthermore, in the example as illustrated in FIG. 16, when a depth amount obtained from the parameter "b(θ, S)" is smaller than a depth limit amount obtained by Formula 2 above, the depth amount obtained from the parameter "b(θ, S)" is displayed on the region R31 as a stereoscopic amount in the depth direction. On the other hand, when the depth amount obtained from the parameter "b(θ, S)" is larger than the depth limit amount, the depth limit amount is displayed on the region R31 as a stereoscopic amount in the depth direction.

It is to be noted that the above-described parameters "a(θ, S)" and "b(θ, S)", and the protrusion limit amount and the depth limit amount may be calculated by the workstation 130, may be calculated by the terminal device 140, or may be set by a manager or the like previously. In any case, the terminal device 140 can display a stereoscopic amount on the region R31 based on the parameters "a(θ, S)" and "b(θ, S)", and the protrusion limit amount and the depth limit amount.

When a predetermined position has been specified through the input unit 141 (double-clicked with a pointing device such as a mouse and a trackball, for example) on any one of the cross-sectional images P11, P12, and P13 on a screen as illustrated in FIG. 16, the terminal device 140 according to the fourth embodiment transmits a focus change request in which the specified position is set to a focus position after changed to the workstation 130.

For example, in the example as illustrated in FIG. 16, it is assumed that a position K1 in the cross-sectional image P11 is double-clicked. In such a case, the request transmitting unit 1452 of the terminal device 140 transmits a focus change request including the position K1 as a focus position after changed to the workstation 130. It is to be noted that since the cross-sectional image corresponds to a cross section of the volume data, the request transmitting unit 1452 can acquire coordinates in the volume data space that correspond to the position K1.

The rendering controller 1352 of the workstation 130 controls the rendering processor 136 so as to perform the rendering processing under a rendering condition that the focus position (position K1) included in the focus change request received from the terminal device 140 is identical to an intersection of sight line directions. Then, the display controller 1353 of the workstation 130 transmits a new parallax image group that has been generated in this manner to the terminal device 140.

The display controller 1451 of the terminal device 140 displays the parallax image group received from the workstation 130 on the stereoscopic display monitor 142. With this, a stereoscopic image on which a focus position is the position K1 is displayed on the stereoscopic display monitor 142. At this time, the display controller 1451 may display a parallax image group such that the position K1 corresponds to a center of the region R21.

It is to be noted that in the above-described example, an example in which a focus position is received in the cross-sectional image P11 as the axial surface has been described. However, the terminal device 140 may receive a focus position in the cross-sectional image P12 of the coronal surface or the cross-sectional image P13 of the sagittal surface.

In addition, the terminal device 140 according to the fourth embodiment can receive change of a stereoscopic amount (size in the depth direction), a region of interest, or a display target region on the flat image P31 that is displayed on the region R31 in FIG. 16. For example, when an operation of changing a stereoscopic amount has been performed, the terminal device 140 transmits a stereoscopic amount after the operation to the workstation 130. An operator moves the straight line L11 or the straight line L12 indicating the stereoscopic amount with a pointing device such as a mouse and a trackball so as to perform the operation of changing the stereoscopic amount.

Furthermore, when a predetermined position has been specified through the input unit 141 (double-clicked with a pointing device such as a mouse and a trackball, for example) on the flat image P31 in FIG. 16, the terminal device 140 transmits a focus change request in which the specified position is set to a focus position after changed to the workstation 130.

Processing of changing a stereoscopic amount or a focus position through the flat image P31 is described with reference to FIGS. 20A to 20D. FIGS. 20A to 20D are views illustrating a display example of a flat image in the fourth embodiment.

Figure 20:
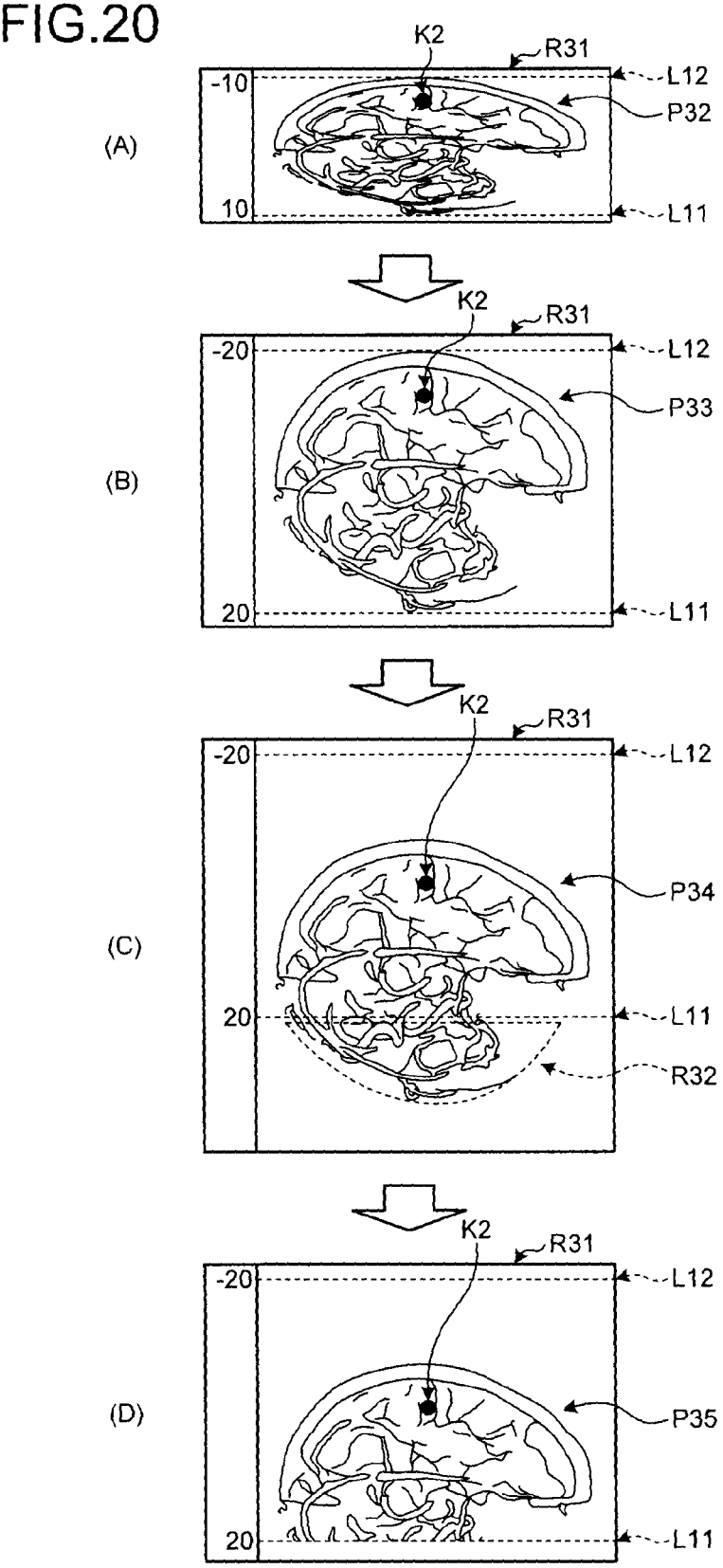
FIG. 20 is a view illustrating a display example of a flat image in the fourth embodiment.

First, it is assumed that an image as illustrated in FIG. 20(A) is displayed on the region R31 as an initial display state. To be more specific, in an example of the FIG. 20(A), the straight line L11 and "10" are displayed as a stereoscopic amount in the protruding direction, and the straight line L12 and "−10" are displayed as a stereoscopic amount in the depth direction. Furthermore, a flat image P32 obtained by seeing the stereoscopic image I21 from the above is displayed on the region R31.

In the state as illustrated in FIG. 20(A), it is assumed that the straight line L11 and the straight line L12 are dragged or the like by an operator and an operation of separating the straight line L11 and the straight line L12 from each other is performed. With this, the terminal device 140 receives a request to change stereoscopic amounts of the stereoscopic image I21 from the operator. It is to be noted that when an operation of moving any one of the straight line L11 and the straight line L12 has been performed, the terminal device 140 also moves the other straight line in conjunction. For example, when a stereoscopic amount of the straight line L11 has been changed from "10" to "20", the terminal device 140 changes a stereoscopic amount of the straight line L12 from "−10" to "−20".

When the stereoscopic amounts have been changed in this manner, the request transmitting unit 1452 of the terminal device 140 transmits stereoscopic amounts indicated by the straight line L11 and the straight line L12 after moved to the workstation 130.

The receiving unit 1351 of the workstation 130 receives the stereoscopic amounts after changed from the terminal device 140. In such a case, the rendering controller 1352 calculates a parallax angle such that the stereoscopic amounts after changed are obtained. To be more specific, the rendering controller 1352 calculates a parallax angle "θ" at which the stereoscopic amounts after changed are obtained using the above-described parameters "a(θ, S)" and "b(θ, S)". Then, the rendering controller 1352 controls the rendering processor 136 so as to perform the rendering processing while the calculated parallax angle is the rendering condition. Thereafter, the display controller 1353 of the workstation 130 transmits a new parallax image group that has been generated in this manner to the terminal device 140.

The display controller 1451 of the terminal device 140 displays the parallax image group received from the workstation 130 on the stereoscopic display monitor 142. With this, a stereoscopic image corresponding to the stereoscopic amounts after changed is displayed on the region R21 as illustrated in FIG. 16. In addition, as illustrated in FIG. 20(B), a flat image P33 corresponding to the stereoscopic amounts after changed is displayed on the region R31.

Furthermore, it is assumed that a position K2 on the flat image P33 has been double-clicked by an operator in the state as illustrated in FIG. 20(B). In such a case, the request transmitting unit 1452 of the terminal device 140 transmits a focus change request including the position K2 as a focus position after changed to the workstation 130. A position in the height direction (y direction) is not obvious only with the position K2. In this example, the request transmitting unit 1452 transmits a position (x coordinate) in the lateral direction and a position (z coordinate) in the depth direction that have been identified by the position K2 to the workstation 130.

The rendering controller 1352 of the workstation 130 controls the rendering processor 136 so as to perform the rendering processing under a rendering condition that the focus position (position K2) included in the focus change request received from the terminal device 140 is identical to an intersection of sight line directions. Then, the display controller 1353 of the workstation 130 transmits a parallax image group that has been generated newly to the terminal device 140.

The display controller 1451 of the terminal device 140 displays the parallax image group received from the workstation 130 on the stereoscopic display monitor 142. With this, a stereoscopic image on which a focus position is the position K is displayed on the region R21 as illustrated in FIG. 16.

At this time, the display controller 1451 may display a parallax image group such that the position K2 corresponds to a center of the region R21. In such a case, as illustrated in FIG. 20(C), the display controller 1451 displays a flat image P34 such that the position K2 corresponds to a center of the region R31.

Furthermore, the terminal device 140 may receive a region to be displayed on the flat image that is displayed on the region R31. For example, in the state as illustrated in FIG. 20(C), a region R32 as a part of the flat image P34 is not included in a range "20" to "−20" of the stereoscopic amounts. There is high possibility that a dimmed image is displayed on the region R32 deviated from the range of the stereoscopic amounts in the stereoscopic image I21. When an operation in which the region R32 is not displayed has been received, the terminal device 140 transmits a display region change request including positional information of a region excluding the region R32 to the workstation 130.

The receiving unit 1351 of the workstation 130 receives the display region change request from the terminal device 140. In such a case, the rendering controller 1352 deletes voxels corresponding to the region (that is, region R32) other than the region indicated by the positional information included in the display region change request in volume data. For example, the rendering controller 1352 updates a voxel value corresponding to the region R32 to a predetermined value indicating the air or the like. Then, the rendering controller 1352 controls the rendering processor 136 so as to perform the rendering processing on the volume data after updated. Thereafter, the display controller 1353 of the workstation 130 transmits the parallax image group that has been generated newly to the terminal device 140.

The display controller 1451 of the terminal device 140 displays the parallax image group that has been received from the workstation 130 on the stereoscopic display monitor 142. With this, a stereoscopic image on which the region R32 has been cut is displayed on the region R21 as illustrated in FIG. 16. Furthermore, as illustrated in FIG. 20(D), a flat image P35 on which the region R32 has been cut is displayed on the region R31.

Thus, in a display mode as illustrated in FIGS. 20A to 20D, an operator can observe details of a portion in the vicinity of the position K2. For example, when the operator desires to observe the details of the position K2 in the state as illustrated in FIG. 20(A), the operator changes the display mode to those as illustrated in FIGS. 20B, 20C, and 20D so as to display the stereoscopic image I21 on which the portion in the vicinity of the position K2 is displayed in detail stereoscopically on the region R21.

It is to be noted that in the example as illustrated in FIGS. 20A to 20D, an example in which the terminal device 140 receives an operation of changing a stereoscopic amount, an operation of changing a focus position, and an operation of specifying a non-display region in this order, and changes a display mode every time each operation is received has been described. However, the terminal device 140 may receive a part or all of the operations collectively and change to a display mode corresponding to the received operations. For example, the terminal device 140 can change from the display mode in FIG. 20(A) to that in FIG. 20(C), or change from the display mode in FIG. 20(A) to that in FIG. 20(D).

Fifth Embodiment

Furthermore, the above-described embodiments can be also varied into other embodiments. In the fifth embodiment, modifications of the above-described embodiments are described.

Cut Display

In the above-described embodiment, the terminal device 140 may display only a focus region of a parallax image group. For example, the terminal device 140 may display only the focus region E11 in the example as illustrated in FIG. 11(A2). In other words, the terminal device 140 may display a parallax image group on which a region other than the focus region has been cut. For example, the terminal device 140 may display only the focus region E11 in the example as illustrated in FIG. 11(A2).

Furthermore, it is not limited thereto and the terminal device 140 may display only a region in the vicinity of a focus region on the parallax image group. For example, the terminal device 140 may display only a region including the focus region E11 and a region in the vicinity of the focus region E11 in the example as illustrated in FIG. 11(A2).

Furthermore, in the above-described second embodiment, the terminal device 140 may display by cutting a region at a side opposite to a travelling direction of the medical device 10 on the parallax images. For example, the terminal device 140 may display by cutting a region at a right side (positive side in the x-axis direction) of the focus region E14 in the example as illustrated in FIG. 13(B3). With this, a physician or the like can observe a stereoscopic image on which a site that needs not be observed has been removed.

It is to be noted that the above-described processing of displaying only a focus region and the like needs not be performed by the terminal device 140, and the rendering controller 1352 or 2352 of the workstation 130 or 230 may generate parallax images on which only the focus region and the like are reflected.

Focus Position

Furthermore, in the above-described embodiments, a case in which the focus position is a straight line in the vertical direction (y direction) mainly has been described as an example. However, the focus position may be a straight line in the lateral direction (x direction) and the depth direction (z direction).

Figure 21:
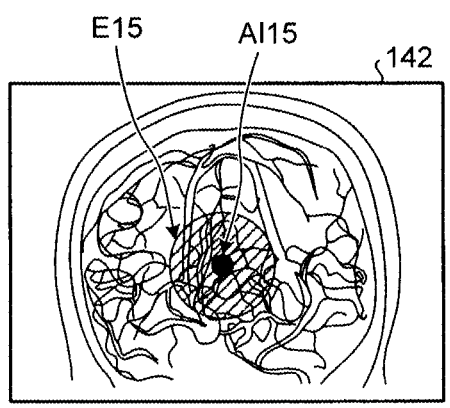
FIG. 21 is a view for explaining a modification of the first to third embodiments.

Furthermore, in the above-described embodiments, a case in which the focus position is a straight line has been described as an example. In this case, it is supposed that when the rendering condition is a perspective projecting method, a viewpoint position is moved on a circular arc about a predetermined straight line (focus position), and when the rendering condition is a parallel projecting method, a viewpoint position is moved in parallel with a straight line perpendicular to the predetermined straight line (focus position). However, the viewpoint position may be moved randomly while the predetermined point (focus position) is set as a center in volume data. That is to say, each viewpoint position at the time of the rendering processing may not be moved regularly (for example, on a circular arc or a straight line) as long as the sight line directions are identical at the predetermined point (focus position). In this case, a focus region on which an undimmed image is not displayed in the stereoscopic image does not have a shape of circular column as illustrated in FIG. 11 but is a focus region E15 having a spherical shape about the focus position as illustrated in FIG. 21, for example. Furthermore, in such a case, as illustrated in FIG. 21, for example, a focus image AI15 having a spherical shape is displayed.

Processing Entity

In the above-described first embodiment, an example in which the terminal device 140 receives an operation of changing a focus position, and displays a parallax image group on which a focus position has been changed on the stereoscopic display monitor 142 has been described. In addition, in the above-described second embodiment, the terminal device 240 displays a parallax image group on which a focus position has been changed with movement of a position of the medical device 10 on the stereoscopic display monitor 142. However, the parallax image group on which a focus position has been changed is not limited to be displayed on the stereoscopic display monitor 142. For example, the workstation 130, 230, or 330 may display the parallax image group on which a focus position has been changed on a display unit 132 as the stereoscopic display monitor.

In addition, in the above-described embodiments, an example in which the terminal device 140 or 240 acquires a parallax image group from the workstation 130, 230, or 330 has been described. However, the terminal device 140 or 240 may have functions that are the same as the controller 135, 235, or 335 and the rendering processor 136 of the workstation 130 and the like. In such a case, the terminal device 140 acquires volume data from the image storage device 120, and performs the same processing as the above-described controller 135, 235, or 335.

Furthermore, in the above-described embodiments, a configuration in which the workstation 130 does not generate a parallax image group from volume data but the medical image diagnostic device 110 has the same function as the rendering processor 136 and generates a parallax image group from the volume data may be employed. In such a case, the terminal device 140 or 240 acquires the parallax image group from the medical image diagnostic device 110.

Parallax Image Number

Furthermore, in the above-described embodiments, an example in which a figure image is superimposed on a parallax image group mainly as nine parallax images so as to be displayed has been described. However, an embodiment is not limited thereto. For example, the workstation 130 may generate a parallax image group as two parallax images.

System Configuration

Furthermore, all of or a part of processing that have been described to be performed automatically among the pieces of processing as described in the above embodiments can be performed manually. Alternatively, all of or a part of processing that have been described to be performed manually among the pieces of processing as described in the above embodiment can be performed automatically by a known method. In addition, information including processing procedures, control procedures, specific names, and various data and parameters as described in the above-described document and drawings can be changed arbitrarily unless otherwise specified.

The constituent components of the devices as illustrated in the drawings are conceptual functionally and are not necessarily required to be configured as illustrated in the drawings physically. That is to say, specific forms of disintegration and integration of the devices are not limited to those as illustrated in the drawings and all of or a part of them can be configured to be disintegrated or integrated functionally or physically based on an arbitrary unit depending on various loads and usage conditions. For example, the controller 135 of the workstation 130 may be connected through a network as an external device of the workstation 130.

Computer Program

Furthermore, a computer program in which processing to be executed by the terminal device 140 or 240 and the workstation 130, 230, or 330 in the above-described embodiments are described with language that can be executed by a computer can be created. In this case, the computer executes the program so as to obtain effects as those obtained in the above-described embodiments. Furthermore, the processing that is the same as that in the above embodiment may be executed by recording the program in a computer readable recording medium and causing the computer to load and execute the program recorded in the recording medium. For example, the program is recorded in a hard disk, a flexible disk (FD), a compact disc read only memory (CD-ROM), a magnetooptic disc (MO), a digital versatile disc (DVD), a Blu-ray (registered trademark) Disc, or the like. Furthermore, the program can be distributed through a network such as the Internet.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing system, comprising:
   a stereoscopic display configured to display a stereoscopic image that is capable of being viewed stereoscopically using a parallax image group as a plurality of parallax images generated by performing rendering processing on volume data being obtained from a scan of an object as three-dimensional medical image data; and
   a processor configured to
   receive a request to change a focus position on the stereoscopic image stereoscopically displayed on the stereoscopic display,
   determine a position of the volume data corresponding to the changed focus position and determine new viewpoint positions of which sight line directions intersect with one another at the determined position of the volume data corresponding to the changed focus position, and
   cause the stereoscopic display to display a new parallax image group that has been generated by performing the rendering processing on the volume data based on the determined new viewpoint positions, a focus of the new parallax image group being the determined position of the volume data corresponding to the changed focus position.

2. The image processing system according to claim 1, wherein
   the processor is further configured to generate the new parallax image group by performing the rendering processing on the volume data based on the determined new viewpoint positions; and
   the processor causes the stereoscopic display to display the generated new parallax image group.

3. The image processing system according to claim 2, further comprising a medical device that is used for a subject present in a three-dimensional space corresponding to a coordinate system of the volume data and on which a position sensor that acquires a position of the medical device in the three-dimensional space is provided, wherein
   the processor receives a position of the medical device acquired by the position sensor as the changed focus position.

4. The image processing system according to claim 2, wherein the processor generates a parallax image group including an image indicating the changed focus position.

5. The image processing system according to claim 2, wherein the processor receives a predetermined three-dimensional region specified in a stereoscopic image space in which a stereoscopic image is displayed by the stereoscopic display as the changed focus position, and
   the processor further determines a parallax angle at which a stereoscopic image is capable of being displayed in the received three-dimensional region, and performs the rendering processing on the volume data further based on the determined parallax angle to generate the new parallax image group.

6. The image processing system according to claim 1, further comprising a memory configured to store a plurality of parallax image groups corresponding to predetermined positions that have been generated by changing the predetermined position and performing the rendering processing a plurality of times by the processor that performs the rendering processing on the volume data based on a plurality of viewpoint positions of which the sight line directions intersect with one another at the predetermined position, wherein the processor acquires a parallax image group corresponding to the determined plurality of viewpoint positions from the memory, and causes the stereoscopic display to display the acquired parallax image group as the new parallax image group.

7. The image processing system according to claim 6, further comprising a medical device that is used for a subject present in a three-dimensional space corresponding to a coordinate system of the volume data and on which a position sensor that acquires a position of the medical device in the three-dimensional space is provided, wherein
the processor receives a position of the medical device acquired by the position sensor as the changed focus position.

8. The image processing system according to claim 6, wherein the processor generates a parallax image group including an image indicating the changed focus position.

9. The image processing system according to claim 1, wherein the processor causes only a region corresponding to the vicinity of the changed focus position in the stereoscopic image to be displayed.

10. The image processing system according to claim 1, wherein the stereoscopic display displays a cross-sectional image obtained from the volume data in parallel together with the stereoscopic image, and
the processor receives the request to change the focus position in the cross-sectional image.

11. The image processing system according to claim 1, wherein the stereoscopic display displays a flat image on which a depth direction of the stereoscopic image is drawn out in parallel together with the stereoscopic image, and
the processor
receives the request to change the focus position, a size in the depth direction, or a display target region on the flat image,
determines a rendering condition on which the received request has been reflected, and
causes the stereoscopic display to display the new parallax image group generated from the volume data under the determined rendering condition on which the received request has been reflected.

12. An image processing device, comprising:
a stereoscopic display configured to display a stereoscopic image that is capable of being viewed stereoscopically using a parallax image group as a plurality of parallax images generated by performing rendering processing on volume data being obtained from a scan of an object as three-dimensional medical image data; and
a processor configured to receive a request to change a focus position on the stereoscopic image stereoscopically displayed on the stereoscopic display, determine a position of the volume data corresponding to the changed focus position and determine new viewpoint positions of which sight line directions intersect with one another at the determined position of the volume data corresponding to the changed focus position, and cause the stereoscopic display to display a new parallax image group that has been generated by performing the rendering processing on the volume data based on the determined new viewpoint positions, a focus of the new parallax image group being the determined position of the volume data corresponding to the changed focus position.

13. An image processing method by an image processing system including a stereoscopic display configured to display a stereoscopic image that is capable of being viewed stereoscopically using a parallax image group as a plurality of parallax images generated by performing rendering processing on volume data being obtained from a scan of an object as three-dimensional medical image data, the image processing method comprising:
receiving, by a processor, a request to change a focus position on the stereoscopic image stereoscopically displayed on the stereoscopic display;
determining a position of the volume data corresponding to the changed focus position and determining new viewpoint positions of which sight line directions intersect with one another at the determined position of the volume data corresponding to the changed focus position, and
causing, by the processor, the stereoscopic display to display a new parallax image group that has been generated by performing the rendering processing on the volume data based on the determined new viewpoint positions, a focus of the new parallax image group being the determined position of the volume data corresponding to the changed focus position.

14. A medical image diagnostic device, comprising:
a stereoscopic display configured to display a stereoscopic image that is capable of being viewed stereoscopically using a parallax image group as a plurality of parallax images generated by performing rendering processing on volume data being obtained from a scan of an object as three-dimensional medical image data; and
a processor configured to receive a request to change a focus position on the stereoscopic image stereoscopically displayed on the stereoscopic display, determine a position of the volume data corresponding to the changed focus position, determine new viewpoint positions of which sight line directions intersect with one another at the determined position of the volume data corresponding to the changed focus position, and cause the stereoscopic display to display a new parallax image group that has been generated by performing the rendering processing on the volume data based on the determined new viewpoint positions, a focus of the new parallax image group being the determined position of the volume data corresponding to the changed focus position.

* * * * *